US010485638B2

(12) United States Patent
Salah et al.

(10) Patent No.: US 10,485,638 B2
(45) Date of Patent: Nov. 26, 2019

(54) METHOD FOR MONITORING DENTITION

(71) Applicant: Dental Monitoring, Paris (FR)

(72) Inventors: Philippe Salah, Bagnolet (FR);
William Ayache, Neuilly-sur-Seine (FR); Laurent Debraux, Paris (FR); Guillaume Ghyselinck, Cantin (FR); Thomas Pellissard, Goussinville (FR)

(73) Assignee: DENTAL MONITORING, Paris (FR)

( * ) Notice: Subject to any disclaimer, the term of this patent is extended or adjusted under 35 U.S.C. 154(b) by 43 days.

(21) Appl. No.: 15/522,520

(22) PCT Filed: Oct. 27, 2015

(86) PCT No.: PCT/EP2015/074896
§ 371 (c)(1),
(2) Date: Apr. 27, 2017

(87) PCT Pub. No.: WO2016/066651
PCT Pub. Date: May 6, 2016

(65) Prior Publication Data
US 2017/0325689 A1 Nov. 16, 2017

(30) Foreign Application Priority Data

Oct. 27, 2014 (FR) .................................... 14 60310
Oct. 27, 2014 (FR) .................................... 14 60315
Mar. 19, 2015 (FR) .................................... 15 52277

(51) Int. Cl.
A61C 9/00 (2006.01)
A61B 5/00 (2006.01)
(Continued)

(52) U.S. Cl.
CPC .......... A61C 9/0053 (2013.01); A61B 5/0088 (2013.01); A61B 5/064 (2013.01);
(Continued)

(58) Field of Classification Search
CPC .......... A61C 1/24; A61C 9/04; A61C 9/0046; A61C 9/0053; A61C 7/00; A61C 7/002;
(Continued)

(56) References Cited

U.S. PATENT DOCUMENTS 5,278,756 A 1/1994 Lemchen et al.
6,328,567 B1 * 12/2001 Morris .................... A61C 19/10
433/203.1
(Continued)

FOREIGN PATENT DOCUMENTS

CA 2292141 A1 6/2001
CN 201244032 Y 5/2009
(Continued)

OTHER PUBLICATIONS

Nov. 21, 2017 Office Action issued in U.S. Appl. No. 15/023,537.
(Continued)

Primary Examiner — Wade Miles
Assistant Examiner — Matthew P Saunders
(74) Attorney, Agent, or Firm — Oliff PLC

(57) ABSTRACT

A method for monitoring a property of the appearance of the teeth of a patient, said method including: A) acquiring, by means of a first acquisition apparatus, at least one first two-dimensional image of said teeth and of a first reference gauge, referred to as "initial image"; B) acquiring, by means of a second acquisition apparatus, at least one second two-dimensional image of said teeth and of a second reference gauge having the same appearance as the first reference gauge, referred to as "updated image"; C) standardising the initial and updated images such that the representations of the first and second reference gauges on the standardised initial and updated images have the same appearance; D) before or after step C, marking the same region of the teeth on the initial and updated images; and E) comparing the
(Continued)

appearance of said region in the standardised initial and updated images.

12 Claims, 7 Drawing Sheets

(51) Int. Cl.
   *A61C 7/00*       (2006.01)
   *A61B 5/06*       (2006.01)
   *G06K 9/00*       (2006.01)
   *G06T 7/33*       (2017.01)
   *G06T 7/73*       (2017.01)
   *G01J 3/00*       (2006.01)
   *G06T 7/55*       (2017.01)
   *G06T 7/246*      (2017.01)
   *G06K 9/62*       (2006.01)
   *G06T 7/00*       (2017.01)
   *G01J 3/50*       (2006.01)
   *G01J 3/52*       (2006.01)
   *A61B 1/32*       (2006.01)
   *A61C 19/06*      (2006.01)
   *A61C 19/10*      (2006.01)
   *A61B 1/00*       (2006.01)
   *A61C 11/00*      (2006.01)

(52) U.S. Cl.
   CPC ............ *A61B 5/4547* (2013.01); *A61B 5/742* (2013.01); *A61C 7/002* (2013.01); *A61C 9/0046* (2013.01); *G01J 3/00* (2013.01); *G01J 3/508* (2013.01); *G01J 3/52* (2013.01); *G06K 9/00* (2013.01); *G06K 9/00214* (2013.01); *G06K 9/6202* (2013.01); *G06T 7/0012* (2013.01); *G06T 7/251* (2017.01); *G06T 7/33* (2017.01); *G06T 7/55* (2017.01); *G06T 7/73* (2017.01); *A61B 1/00009* (2013.01); *A61B 1/32* (2013.01); *A61B 2576/02* (2013.01); *A61C 11/00* (2013.01); *A61C 19/066* (2013.01); *A61C 19/10* (2013.01); *A61C 2007/004* (2013.01); *G06K 2209/05* (2013.01); *G06T 2207/30004* (2013.01); *G06T 2207/30036* (2013.01)

(58) Field of Classification Search
   CPC ............... A61C 2007/004; H04N 1/00; G06T 7/00–251; G06T 2207/30036; G06K 2209/05; G06F 19/3418; G06F 19/3481; G06F 17/50; G06F 3/011; A61B 5/4547; A61B 6/14; A61B 6/145; G01J 3/463; G01J 3/503
   USPC .......................................................... 433/24
   See application file for complete search history.

(56)  References Cited

U.S. PATENT DOCUMENTS 6,431,870 B1      8/2002   Sachdeva
   6,793,489 B2 *    9/2004   Morris ................... A61C 19/10
                                                                    356/404
   8,562,338 B2     10/2013   Kitching et al.
   8,684,729 B2      4/2014   Wen
   8,998,609 B2      4/2015   Prakash et al.
   9,572,637 B2      2/2017   Jinkyun
   9,861,451 B1      1/2018   Davis
   2002/0015934 A1*  2/2002   Rubbert .................. A61C 7/00
                                                                    433/29
   2003/0224314 A1  12/2003   Bergersen
   2004/0038168 A1*  2/2004   Choi ........................ A61C 7/00
                                                                    433/24
   2004/0197727 A1  10/2004   Sachdeva et al.
   2004/0252303 A1* 12/2004   Giorgianni ................ G01J 3/50
                                                                    356/402
   2005/0048432 A1   3/2005   Choi et al.
   2005/0123180 A1*  6/2005   Luo ......................... G01J 3/50
                                                                    382/128
   2006/0127854 A1   6/2006   Wen
   2006/0136267 A1   6/2006   Brackett et al.
   2006/0177789 A1   8/2006   O'Bryan
   2006/0199140 A1   9/2006   Wen
   2006/0199142 A1   9/2006   Liu et al.
   2008/0306724 A1  12/2008   Kitching et al.
   2008/0318179 A1  12/2008   Liu
   2009/0291417 A1  11/2009   Rubbert et al.
   2010/0042440 A1   2/2010   Joao
   2013/0017506 A1   1/2013   Parker
   2013/0044932 A1   2/2013   Caligor et al.
   2013/0059262 A1   3/2013   Farrell
   2013/0215383 A1   8/2013   Siminou
   2013/0286174 A1  10/2013   Urakabe
   2013/0345524 A1  12/2013   Meyer et al.
   2014/0147807 A1   5/2014   Yau et al.
   2014/0204118 A1*  7/2014   Berry .................... G06T 19/006
                                                                    345/633
   2014/0221819 A1   8/2014   Sarment
   2014/0379356 A1  12/2014   Sachdeva et al.
   2015/0127266 A1   5/2015   Chen
   2015/0157209 A1   6/2015   Dantus
   2015/0320320 A1  11/2015   Kopelman et al.
   2016/0004811 A1   1/2016   Somasundaram et al.
   2016/0012182 A1   1/2016   Golay
   2016/0220105 A1   8/2016   Duret
   2016/0228212 A1   8/2016   Salah et al.
   2018/0055600 A1   3/2018   Matov et al.

FOREIGN PATENT DOCUMENTS

EP           3050534 A1       8/2016
   FR           1460310 A       11/1966
   FR           3010629 A1       3/2015
   JP           5241971 B1       7/2013
   KR     10-2018-0008532 A      1/2018
   WO        2001/051005 A2      7/2001
   WO        2006/065955 A2      6/2006
   WO     WO-2006065955 A2 *     6/2006  ........... A61B 5/1111
   WO        2013/090843 A1      6/2013
   WO        2017/182648 A1     10/2017
   WO        2017/182654 A1     10/2017

OTHER PUBLICATIONS

Krieger, "It's not about the dental camera . . . ," Blog. Dental Photography Pearls for Better Images Instantly. Blogspot, Mar. 14, 2012, Published. Web., Nov. 9, 2017 Accessed. <http://dentalphotography.blogspot.com/2012/03/its-not-aboutcamera_14.html#WgTKKzN950R>.
Jul. 3, 2018 Office Action issued in U.S. Appl. No. 15/522,576.
May 30, 2018 Office Action issued in U.S. Appl. No. 15/522,606.
Dec. 8, 2014 Search Report issued in International Patent Application No. PCT/IB2014/064658.
Dec. 8, 2014 Written Opinion issued in International Patent Application No. PCT/IB2014/064658.
Apr. 7, 2017 Office Action Issued in U.S. Appl. No. 15/023,537.
Braces Guide: Retainer Check Appointments (2015).
Fleischmann, Georg, "Cenon: The CAM User's Guide, Version 4.0", http://www.Cenon.com, pp. 1-174 (2014).
Toet, Alexander, "Target Detection and Recognition through Contour Matching", CALMA Report CALMA.TNO.WP31.AT.95b, pp. 1-32 (1994).
"Smile Capture", Style Italiano, www.styleitaliano.org/smile-capture/, pp. 1-20, 2014 (retrieved Aug. 8, 2015).
Ahmad, Irfan, "Digital dental photography Part 8: intra-oral set-ups", British Dental Journal, vol. 207, pp. 151-157 (2009).
U.S. Appl. No. 15/023,537, filed Mar. 21, 2016 in the name of Salah et al.

(56) References Cited

OTHER PUBLICATIONS

Jan. 7, 2016 Written Opinion issued in International Patent Application No. PCT/EP2015/074895.
U.S. Appl. No. 15/522,523, filed Apr. 27, 2017 in the name of Salah et al.
Jan. 12, 2016 Written Opinion issued in International Patent Application No. PCT/EP2015/074896.
Feb. 24, 2016 Written Opinion issued in International Patent Application No. PCT/EP2015/074868.
U.S. Appl. No. 15/522,576, filed Apr. 27, 2017 in the name of Salah et al.
Jan. 26, 2016 Written Opinion issued in International Patent Application No. PCT/EP2015/074897.
U.S. Appl. No. 15/522,554, filed Apr. 27, 2017 in the name of Salah et al.
Jan. 13, 2016 Written Opinion issued in International Patent Application No. PCT/EP2015/074900.
U.S. Appl. No. 15/522,430, filed Apr. 27, 2017 in the name of Salah et al.
Feb. 18, 2016 Written Opinion issued in International Patent Application No. PCT/EP2015/074859.
U.S. Appl. No. 15/522,606, filed Apr. 27, 2017 in the name of Salah et al.
Jun. 24, 2019 Office Action issued in U.S. Appl. No. 15/023,537.
Dec. 18, 2018 Office Action issued in U.S. Appl. No. 15/023,537.
Jan. 4, 2019 Office Action issued in U.S. Appl. No. 15/522,576.
Ralls, et al., "Computer-Assisted Dental Diagnosis," Dental Clinics of North America, vol. 30, No. 4, Oct. 1986, pp. 695-712.
U.S. Appl. No. 16/094,245, filed Oct. 17, 2018 in the name of Salah et al.
U.S. Appl. No. 16/094,255, filed Nov. 9, 2018 in the name of Salah et al.
U.S. Appl. No. 15/990,950, filed May 29, 2018 in the name of Salah et al.
U.S. Appl. No. 16/001,049, filed Jun. 6, 2018 in the name of Salah et al.
U.S. Appl. No. 16/031,201, filed Jul. 10, 2018 in the name of Salah et al.
Taner, et al., "Evaluation of dental arch width and form changes after orthodonic treatment and tention with a new computerized method," American Journal of Orthodontics and Dentofacial Orthopedics, vol. 126, No. 4, Oct. 2004. pp. 464-475.
Nov. 29, 2018 Office Action issued in U.S. Appl. No. 15/522,554.
Aug. 1, 2019 Office Action Issued in U.S. Appl. No. 15/522,523.
Aug. 8, 2019 Office Action Issued in U.S. Appl. No. 15/522,554.

* cited by examiner

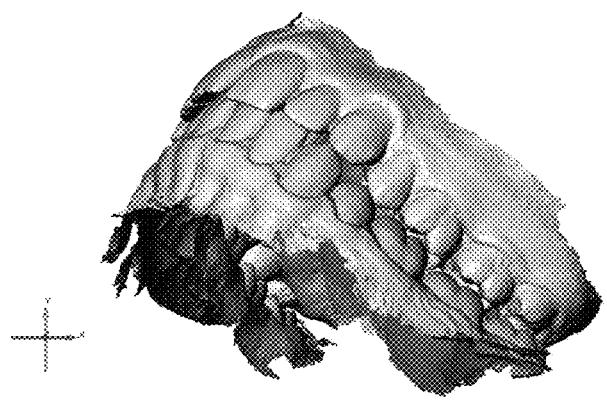
Fig. 2
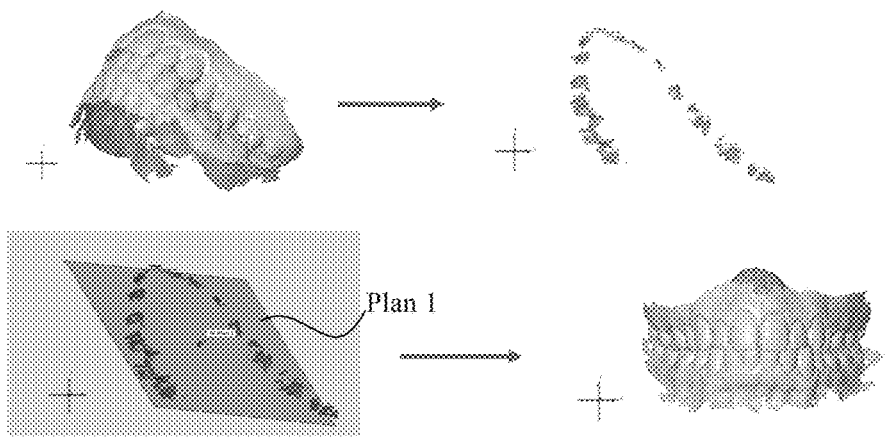
Fig. 3
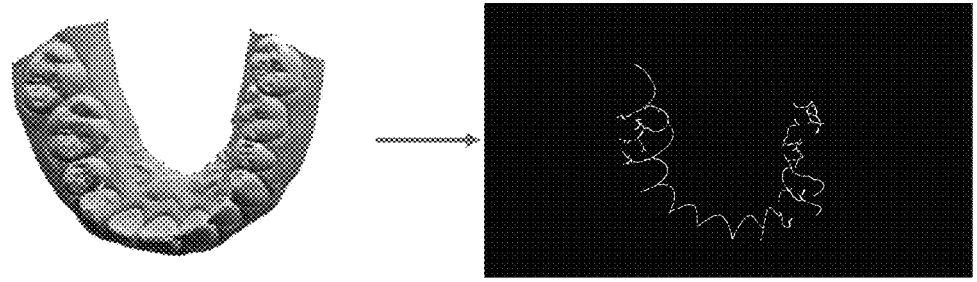
Fig. 4a                    Fig. 4b

20

METHOD FOR MONITORING DENTITION

TECHNICAL FIELD

The present invention relates to a method for monitoring the positioning and/or the shape and/or the appearance of teeth of a patient and a computer program for implementing this method.

STATE OF THE ART

It is desirable for each person to have his or her dentition checked regularly, particularly in order to check that the position and/or the shape and/or the appearance of his or her teeth is not changing for the worse.

During orthodontic treatment, this change for the worse can notably lead to a change of treatment. After an orthodontic treatment, this change for the worse, called "recurrence", can lead to a resumption of a treatment. Finally, more generally and independently of any treatment, each person may want to track any movement and/or the changing shape and/or appearance of his or her teeth.

Conventionally, the checks are performed by an orthodontist or a dentist who alone have appropriate apparatus. These checks are therefore costly. Furthermore, the visits are restrictive.

US 2009/0291417 describes a method making it possible to create, then modify, three-dimensional models, notably for the production of orthodontic appliances.

One aim of the present invention is to address, at least partially, the abovementioned problems.

SUMMARY OF THE INVENTION

The invention provides a method for monitoring the positioning and/or the shape of the teeth of a patient, said method comprising the following steps:
  a) production of a three-dimensional digital reference model of at least part of an arch, preferably of at least one arch of the patient, or "initial reference model" and, preferably, for each tooth, definition, from the initial reference model, of a three-dimensional digital reference model of said tooth, or "tooth model";
  b) acquisition of at least one two-dimensional image of the arches of the patient, called "updated image", in actual acquisition conditions;
  c) analysis of each updated image and production, for each updated image, of an updated map relating to a discriminating piece of information;
  d) optionally, determination, for each updated image, of rough virtual acquisition conditions approximating said actual acquisition conditions;
  e) searching, for each updated image, for a final reference model corresponding to the positioning and/or the shape of the teeth during the acquisition of the updated image, the search being preferably performed by means of a metaheuristic method, preferably evolutionist, preferably by simulated annealing, and
  f) for each tooth model, comparison of the positionings of said tooth model in the initial reference model and in the reference model obtained at the end of the preceding steps, called "final reference model", in order to determine the movement of the teeth between the steps a) and b), and/or
  comparison of the shapes of the initial reference model and of the reference model obtained at the end of the preceding steps, called "final reference model", in order to determine the deformation and/or the movement of the teeth between the steps a) and b).

As will be seen in more detail hereinbelow in the description, a method for monitoring the positioning and/or the shape of teeth according to the invention makes it possible, from a simple image of the teeth, taken without precise prepositioning of the teeth relative to the image acquisition apparatus, for example from a photograph taken by the patient, to assess accurately the movement and/or the deformation of the teeth from the production of the initial reference model. This assessment can also be performed by a simple computer, a server or a mobile phone.

Preferably, the step e) comprises:
  a first optimization operation making it possible to search for the virtual acquisition conditions best corresponding to the actual acquisition conditions in a reference model to be tested determined from the initial reference model, and
  a second optimization operation making it possible to search for, by testing a plurality of said reference models to be tested, the reference model best corresponding to the positioning and/or the shape of the teeth of the patient during the acquisition of the updated image in the step b).

Preferably, a first optimization operation is performed for each test of a reference model to be tested during the second optimization operation.

Preferably, the first optimization operation and/or the second optimization operation, preferably the first optimization operation and the second optimization operation, implement a metaheuristic method, preferably evolutionist, preferably a simulated annealing.

Preferably, the step e) comprises the following steps:
  e1) definition of a reference model to be tested as being the initial reference model then,
  e2) according to the following steps, testing of the virtual acquisition conditions with the reference model to be tested in order to finely approximate said actual acquisition conditions;
    e21) determination of virtual acquisition conditions to be tested;
    e22) production of a two-dimensional reference image of the reference model to be tested in said virtual acquisition conditions to be tested;
    e23) processing of the reference image to produce at least one reference map representing, at least partially, said discriminating piece of information;
    e24) comparison of the updated and reference maps so as to determine a value for a first assessment function, said value for the first assessment function depending on the differences between said updated and reference maps and corresponding to a decision to continue or to stop the search for virtual acquisition conditions approximating said actual acquisition conditions with greater accuracy than said virtual acquisition conditions to be tested determined on the last occurrence of the step e21);
    e25) if said value for the first assessment function corresponds to a decision to continue said search, modification of the virtual acquisition conditions to be tested, then return to the step e22);
  e3) determination of a value for a second assessment function, said value for the second assessment function depending on the differences between the updated and reference maps in the virtual acquisition conditions best approximating said actual acquisition conditions and resulting from the last occurrence of the step e2), said value for the second assessment function corresponding to a decision to continue or to stop the search for a reference model approximating the shape and/or the positioning of the teeth during the acquisition of the updated image with greater accuracy than said reference model to be tested used on the last occurrence of the step e2), and if said value for the second assessment function corresponds to a decision to continue said search, modification of the reference model to be tested by deformation of the reference model to be tested and/or by movement and/or deformation of one or more tooth models, then return to the step e2).

A method for monitoring the positioning and/or the shape of teeth according to the invention can also comprise one or more of the following optional features:

- in the step a), an occlusal plane is determined according to the following operations:
  - I. determination of the points of the initial reference model which belong to an arch and which are at a distance from the other arch which is less than a predetermined distance, preferably at a distance less than 3 mm from the other arch, called "points of contact";
  - II. optionally, filtering of some of the points of contact, preferably such that the number of points of contact belonging to the upper arch is identical to the number of points of contact belonging to the lower arch, preferably by eliminating the points of an arch that are furthest away from the other arch;
  - III. linear regression, preferably by the least squares method, over all the points of contact remaining so as to determine the occlusal plane;
- in the step a), the following operations are performed:
  - i. projection, in an occlusal plane, of the points of contact between the teeth of the upper and lower arches of the patient, the points of contact and/or the occlusal plane being preferably determined, according to steps I to III;
  - ii. determination of the barycenter of the projections of said points of contact and creation of a reference frame, in the occlusal plane, centered on said barycenter;
  - iii. determination, in said reference frame, of the parabolic function exhibiting the greatest coefficient of correlation with all the projections of the points of contact;
  - iv. rotation of all the projections of the points of contact about the barycenter, and repeating of the preceding operation iii until all the projections of the points of contact have covered a determined sector, preferably greater than 90°, greater than 180°, even approximately 360°;
  - v. identification of the highest coefficient of correlation for all the angular positions of all the projections of the points of contact about the barycenter, and of the axis of the corresponding parabolic function;
  - vi. determination of a median longitudinal plane of the initial reference model, said plane passing through said axis and being at right angles to the occlusal plane;
- in the step a), a tooth model is at least partially delimited according to the following operations:
  - i'. determination, at least partially, of interior and exterior gingival edges of the arch of the tooth concerned, preferably by analysis of the variations of the orientation of the surface of the initial reference model;
  - ii'. projection, in the occlusal plane, of the interior and exterior gingival edges;
  - iii'. identification of the deformations of the projections of the interior and exterior gingival edges corresponding to interdental regions, the tops of these deformations being called "point of convergence" (in an interdental region, the two projections each have a point, the two points pointing substantially toward one another, the end of one point being a point of convergence);
  - iv'. determination of the shortest path, on the surface of the initial reference model, between two points of convergence of interior and exterior gingival edges, respectively, of an interdental region, preferably by a metaheuristic method, preferably evolutionist, preferably by simulated annealing, said shortest path at least partially delimiting a tooth model;
- an updated image is acquired less than seven days after the step a), then the steps c) to f) are implemented from this updated image;
- the time interval between the steps a) and b) or between the steps A and B can be greater than one week, than two weeks, than one month, than two months or than six months;
- in the step b), a hand-held acquisition apparatus is used (and in particular one which is not immobilized, for example by means of a support resting on the ground) and/or the head of the patient is not immobilized;
- an individual apparatus is used that is chosen from the group formed by a connected camera, a smart watch, a digital tablet, a portable 3D scanner and a computer coupled to an image acquisition system, such as a webcam or a digital camera, to implement the step b) and, preferably at least one of the steps, preferably all of the steps c) to f);
- in the step b), a separator is used comprising one, preferably more than two register marks, preferably non-aligned, and, preferably, the representation of the register marks on the updated image is used to
  - in the step c), recut the image and/or,
  - in the step d), roughly assess the actual acquisition conditions;
- in the step c), the discriminating piece of information is chosen form the group consisting of a piece of outline information, a piece of color information, a piece of density information, a piece of distance information, a piece of brightness information, a piece of saturation information, a piece of information on glare and combinations of the above pieces of information;
- in the step c), the discriminating piece of information is an optimum piece of discriminating information obtained by means of an optimization method according to the invention, described hereinbelow;
- in the step d), data supplied by the acquisition apparatus and, preferably, concerning its orientation, are used;
- in the step e2), the virtual acquisition conditions sought comprise calibration parameters of the acquisition apparatus implemented in the step b);
- an optimization is implemented by a metaheuristic method, preferably evolutionist, preferably by simulated annealing to:
  - in the step a), at least partially determine a gingival edge delimiting a tooth model, and/or
  - in the step e2), search for the virtual acquisition conditions corresponding to the actual acquisition conditions, and/or in the step e), search for a reference model corresponding to the updated image;
said metaheuristic method is chosen from the group formed by
the evolutionist algorithms, preferably chosen from: evolution strategies, genetic algorithms, differential evolution algorithms, distribution estimation algorithms, artificial immunity systems, Shuffled Complex Evolution path recomposition, simulated annealing, ant colony algorithms, particle swarm optimization algorithms, taboo search, and the GRASP method;
the kangaroo algorithm,
the Fletcher and Powell method,
the noise method,
stochastic tunneling,
hill climbing with random restarts,
the cross entropy method, and
hybrids of the metaheuristic methods described above;
from the comparison in the step f), a mapping is produced showing the changes of shape of the initial reference model and/or the movement of one or more tooth models;
the discriminating information used for the updated map and/or for the reference map is, prior to this use, optimized by means of an optimization method according to the invention described hereinbelow, comprising steps C1 to C3, the image acquired being the updated image or the reference image, respectively, and the reference model being the initial reference model or the reference model to be tested, respectively.

The invention also relates to the use of a method for monitoring the positioning of teeth according to the invention for
detecting a recurrence, and/or
determining a rate of evolution of a change of positioning of the teeth, and/or
optimizing the date on which an appointment is made with an orthodontist or a dentist, and/or
assessing the effectiveness of an orthodontic treatment, and/or
assessing the evolution of the positioning of teeth toward a theoretical model corresponding to a determined positioning of the teeth, in particular an enhanced positioning of the teeth, and/or
dentistry.

The method can notably be implemented during an orthodontic treatment, notably to monitor the progress thereof, the step a) being implemented less than three months, less than two months, less one month, less than one week, less than two days after the start of the treatment, that is to say after the fitting of an appliance intended to correct the positioning of the teeth of the patient, called "active retaining appliance".

The method can also be implemented after an orthodontic treatment, to check that the positioning of the teeth does not evolve unfavorably ("recurrence"). The step a) is then preferably implemented less than three months, less than two months, less than one month, less than one week, less than two days after the end of the treatment, that is to say after the fitting of an appliance intended to hold the teeth in position, called "passive retaining appliance".

In one embodiment, to monitor exclusively the movement of the teeth, it is considered that tooth models are non-deformable during the step e). In particular, in the step e3), the reference model to be tested can be modified only by movement of one or more tooth models.

The invention relates also to the use of a method for monitoring the shape of teeth according to the invention for:
displaying and/or measuring and/or detecting dental plaque, and/or a start of caries, and/or a microcracking, and/or wear, for example resulting from bruxism or from the implementation of an orthodontic appliance, active or passive, notably in case of breakage or of detachment of an orthodontic arc;
displaying and/or measuring and/or detecting a change of volume, in particular during the growth of the teeth or following an intervention of a dentist or of an orthodontist, for example a deposit of glue on the surface of the teeth;
assessing advisability of an interceptive treatment, before any orthodontic treatment, notably to assess the benefit of an orthodontic treatment.

In one embodiment, to monitor exclusively the deformation of the teeth, it is considered, during the step e), that the tooth models are fixed, that is to say have not moved between the steps a) and b). In particular, in the step e3), the reference model to be tested can be modified only by deformation of one or more tooth models.

The comparison of the shapes of the initial reference model and of the final reference model in order to determine the deformation of teeth between the steps a) and b) can in particular result from a comparison of the shape of one or more tooth models in the initial reference model and in the final reference model.

The invention relates also to a method for monitoring a property of appearance of teeth of a patient, said method comprising the following successive steps:
A. acquisition, by means of a first acquisition apparatus, of at least one first two-dimensional image of said teeth and of a first reference gauge, called "initial image";
B. acquisition, by means of a second acquisition apparatus, of at least one second two-dimensional image of said teeth and of a second reference gauge exhibiting a same appearance as the first reference gauge, called "updated image";
C. normalization of the initial and updated images so that the representations of the first and second reference gauges on the normalized initial and updated images exhibit a same appearance;
D. before or after the step C., identification of a same region of the teeth on the initial and updated images;
E. comparison of the appearance of said region on the normalized initial and updated images.

A method for monitoring a tooth appearance property according to the invention preferably comprises one or more of the following optional features:
the time interval between the steps A. and B. is greater than one week;
the first acquisition apparatus and/or the second acquisition apparatus are cameras and/or mobile phones;
the acquisitions in the steps A. and/or B. are performed under flash lighting;
the reference gauges used for each of the steps A. and B. exhibit a same appearance;
the reference gauges used for each of the steps A. and B. are set on a dental separator;
the acquisitions in the steps A. and/or B. are performed by means of an acquisition kit according to the invention, described hereinbelow;
the reference gauges used for each of the steps A. and B. are register marks;
the first acquisition apparatus and/or the second acquisition apparatus comprises a computer program comprising program code instructions for identifying, in real time, the register mark or marks on the separator, analyzing its or their positions and/or dimensions, in particular the relative positons of several register marks and, accordingly, supplying a piece of information, preferably light-based or sound-based, so as to inform the user of said acquisition apparatus;

in the step D., the identification comprises a comparison of discriminating pieces of information common to both the initial and the updated image, then an identification of the position of said region relative to said common discriminating pieces of information;

in the step D., the identification of the region on the initial and/or updated images comprises a search for virtual acquisition conditions in which the first and/or second acquisition apparatuses, respectively, would have acquired said initial and/or updated image, respectively, by observing a three-dimensional digital reference model of the arches of the patient.

in the step D., the identification of the region on the initial and/or updated images comprises the implementation of a method for assessing the actual acquisition conditions according to the invention, described hereinbelow.

The invention also relates to an acquisition kit, notably for implementing a step b), A. or B., said acquisition kit comprising:

a dental separator intended to be placed in the mouth of a patient and comprising a register mark;

an image acquisition apparatus comprising;

a display screen, a computer memory containing information on target acquisition conditions, a computer program comprising program code instructions for simultaneously displaying, on said screen, a preview image and a reference, said reference being in a position such that, when the register mark matches the reference on the screen, the acquisition apparatus meets the target acquisition conditions.

An acquisition kit according to the invention can notably be implemented in the step b) of a method for monitoring the positioning and/or the shape of the teeth according to the invention, or in the steps A. and/or B. of a method for monitoring a tooth appearance property, and more generally, for any method comprising an assessment of the acquisition conditions of an image.

As will be seen in more detail hereinbelow in the description, an acquisition kit according to the invention makes it possible in particular to position the acquisition apparatus in a position which corresponds substantially to a predetermined position, for example considered as optimal for the desired monitoring. An acquisition kit according to the invention therefore makes it possible to considerably improve the information processing speed for the implementation of the monitoring methods according to the invention.

An acquisition kit according to the invention preferably has one or more of the following optional features:

the acquisition apparatus is a mobile phone;

the reference is chosen from the group consisting of
 a point,
 a geometrical shape, preferably a circle, a square, a rectangle or a line,
 a colored zone of the same color as said register mark,
 a shape identical to the shape of said register mark,
 a shape complementing the shape of said register mark, in particular to form a shape having a direction, like a geometrical shape, a letter or a text, a drawing, or a pattern, and
 their combinations;

the separator comprises several non-aligned register marks, and preferably coplanar;

the register mark is arranged so that, when it matches said reference on the screen, it is less than 1 cm from an edge of the screen.

The invention relates also to a method for acquiring a two-dimensional image of a part of a dental arch, or of a dental arch or of the two dental arches of a patient by means of an acquisition kit according to the invention, notably for the implementation of a step b), A. and/or B. This method is noteworthy in that it comprises the following successive steps:

(a) determination of target acquisition conditions, for example according to a treatment to be applied, in particular an orthodontic treatment, and determination of conditions of match suitable for a matching of a register mark of the separator with a reference displayed on the screen of the acquisition apparatus to result in the application of the target acquisition conditions;

(b) programming of the acquisition apparatus so as to display the reference in a position such that said matching results in the application of the target acquisition conditions;

(c) placement of the separator in the mouth of the patient;

(d) positioning of the acquisition apparatus so as to match the register mark and the reference and thus apply the target acquisition conditions;

(e) acquisition of the preview image in the positioning of the acquisition apparatus adopted in the preceding step.

The target acquisition conditions are conditions allowing a suitable positioning of the acquisition apparatus, preferably an optimum positioning of the acquisition apparatus for acquiring the image. Preferably, the target acquisition conditions are therefore determined according to the teeth to be observed.

Preferably, an acquisition method according to the invention is implemented for the steps of the monitoring methods according to the invention requiring the acquisition of a two-dimensional image of a part of an arch or of a dental arch or of both dental arches of a patient, and in particular for the steps b).

Preferably, the cycle of the steps (a) to (e) is repeated several times, preferably more than two times, even more than three times, with different target acquisition conditions.

For example, to measure the movement of a tooth, first target acquisition conditions will be able to correspond to a positioning at 40 cm from the separator, facing and at the same height as the separator. Second and third target acquisition conditions will be able to correspond to a positioning at 40 cm from the separator, at the same height as the separator, at 45° to the right and to the left of the saggital plane, respectively.

Preferably, the steps (c), (d) and (e) are executed by a person without any university training in orthodontics and/or outside of any medical, dentistry or orthodontics practice, and/or without recourse to a device for mechanically stabilizing the acquisition apparatus and/or without recourse to appliances other than a mobile phone and/or without recourse to a standard calibration gauge.

The invention relates also to a method for optimizing a discriminating piece of information extracted from a two-dimensional image of the dental arches of a patient, called "acquired image", by means of a three-dimensional digital reference model of at least a part of an arch of the patient, or of an arch or of the two arches of the patient, said method comprising the following steps:

C1. assessment of the quality of the discriminating piece of information and of a quality threshold, filtering so as to retain only the discriminating piece of information exhibiting a quality above the quality threshold, and definition of the "discriminating piece of information to be tested" as being the discriminating piece of information retained;

C2. testing of a match between the discriminating piece of information to be tested and said reference model;

C3. assessment of the result of the test, and, based on said assessment:
   addition of discriminating information not retained to the discriminating piece of information to be tested and/or elimination of discriminating information from the discriminating piece of information to be tested, then return to the step C2., or,
   definition of the optimum discriminating piece of information as being the discriminating piece of information to be tested.

Preferably, an optimization method according to the invention also comprises one or more of the following optional features:

the discriminating information is chosen from the group consisting of a piece of outline information, a piece of color information, a piece of density information, a piece of distance information, a piece of brightness information, a piece of saturation information, a piece of information on glare, and combinations of these pieces of information;

the step C2. comprises the following steps:
   search for virtual acquisition conditions approximating, preferably optimally, actual acquisition conditions in which said acquired image was acquired and observation of the reference model in said virtual acquisition conditions so as to obtain a reference image;
   processing of the acquired image and of the reference image to produce at least one acquired map and one reference map, respectively, said acquired and reference maps representing said discriminating information;
   comparison of the acquired and reference maps to determine a degree of match, the result of the test of the step C2. depending on, preferably being equal to, said degree of match;

the search for virtual acquisition conditions approximating the actual acquisition conditions comprises the following steps:
   01) optionally, determination of rough virtual acquisition conditions approximating said actual acquisition conditions, preferably by analysis of the representation, on the acquired image, of a separator used during the acquisition of the acquired image;
   02) determination of virtual acquisition conditions to be tested;
   03) production of a two-dimensional reference image of the reference model observed in the virtual acquisition conditions to be tested;
   04) processing of the reference image to produce at least one reference map representing said discriminating information;
   05) comparison of the acquired and reference maps so as to determine a value for an assessment function,
   said value for the assessment function depending on the differences between said acquired and reference maps and corresponding to a decision to continue or to stop the search for virtual acquisition conditions approximating the actual acquisition conditions with greater accuracy than said virtual acquisition conditions to be tested;
      if said value for the assessment function corresponds to a decision to continue said search, modification of said virtual acquisition conditions to be tested, then return to the step 03);
      otherwise, assessment of the actual acquisition conditions by said virtual acquisition conditions to be tested;
   the determination of the discriminating information to be added and/or to be added in the step C3. results from the implementation of a metaheuristic method, preferably evolutionist.

The invention relates also to a method for assessing actual acquisition conditions of a two-dimensional image of the teeth of a patient, called "acquired image", said method comprising the following steps:
   001) production of a three-dimensional digital reference model of at least a part of an arch, preferably of an arch, preferably of the two arches of the patient;
   002) analysis of the acquired image and production of a map relating to a discriminating piece of information, called "acquired map";
   003) search for the virtual acquisition conditions approximating said actual acquisition conditions, preferably according to the steps 01) to 05).

One or more of the features, possibly optional, of the step a) are applicable to the step 001). In particular, the reference model can be prepared, by a scan, from measurements performed on the teeth of the patient or on a physical model of his or her teeth, for example a plaster model.

One or more of the features, possibly optional, of the step c) are applicable to the step 002).

The invention also relates to:
   a computer program, and in particular an application specifically for mobile phones, comprising program code instructions for the execution of one or more, preferably all, of the steps b) to f) or A. to E., or C1 to C3, when said program is run by a computer,
   a computer medium on which is stored such a program, for example a memory or a CD-ROM, and
   a personal appliance, in particular a mobile phone or a tablet, in which such a program is loaded.

The invention relates also to a system comprising
   a three-dimensional scanner capable of implementing the step a) of a method for monitoring the positioning and/or the shape of teeth according to the invention, or a step 001).
   a personal appliance, preferably a mobile phone, loaded with a program according to the invention.

Definitions

A "patient" should be understood to mean any person for whom a method is implemented in order to monitor the teeth thereof, whether this person is sick or not, or whether this person is currently being treated or not.

A "dental health professional" should be understood to mean a dentist, an orthodontist or an orthodontic laboratory.

A "dentist" should be understood to be a dentist or a dental assistant working under the responsibility of a dentist.

"Dentition" should be understood to mean the two dental arches of the patient.

An image of an arch is of course a partial representation of this arch.

A "mobile phone" is an appliance weighing less than 500 g, provided with a sensor enabling it to capture images, capable of exchanging data with another appliance more than 500 km away from the mobile phone, and capable of displaying said data, and notably said images.

For a method for monitoring the positioning of the teeth, the "acquisition conditions" specify the position and the orientation in space of an image acquisition apparatus in relation to the teeth of the patient or to a tooth model of the patient, and preferably the calibration of this image acquisition apparatus.

The "calibration" of an acquisition apparatus is made up of all the values of the calibration parameters. A calibration parameter is a parameter intrinsic to the acquisition apparatus (unlike its position and its orientation), the value of which influences the image acquired. For example, the diaphragm aperture is a calibration parameter which modifies the depth of field. The exposure time is a calibration parameter which modifies the brightness (or "exposure") of the image. The focal distance is a calibration parameter which modifies the viewing angle, that is to say the degree of "zoom". The "sensitivity" is a calibration parameter which modifies the response of the sensor of a digital acquisition apparatus to the incident light.

Preferably, the calibration parameters are chosen from the group formed by the diaphragm aperture, the exposure time, the focal distance and the sensitivity.

The "occlusal plane" is the plane which provides the best linear correlation with all the points of contact between the teeth of the upper arch on the one hand and the teeth of the lower arch on the other hand.

The "median longitudinal plane" is the plane substantially vertical when the patient holds the head straight, which substantially symmetrically separates left and right parts of each arch.

A "tablet" is a portable computer with touchscreen.

A 3D scanner is an apparatus making it possible to obtain a three-dimensional representation of an object.

An "image" is understood to be a two-dimensional image, like a photograph. An image is formed by pixels.

A "preview" image is the image that the acquisition apparatus can record at a given instant. For a camera or a telephone, it is the image which appears on screen when the photo or video acquisition application is running.

A "discriminating piece of information" is a characteristic information which can be extracted from an image ("image feature"), conventionally by a computer processing of this image.

A discriminating piece of information can have a variable number of values. For example, an outline information can be equal to one or zero depending on whether a pixel belongs or does not belong to an outline. A brightness information can take a large number of values.

The processing of the image makes it possible to extract and quantify the discriminating information.

Acquisition conditions are called "virtual" when they correspond to a simulation in which the acquisition apparatus would be in said acquisition conditions (theoretical positioning and preferably calibration of the acquisition apparatus).

"Comprising a" or "including a" or "having a", should be understood to mean "including at least one", unless indicated otherwise.

In the different methods described, the references of the steps are identical if these steps are similar or identical.

BRIEF DESCRIPTION OF THE FIGURES

Other features and advantages of the invention will become more apparent on reading the following detailed description and on studying the attached drawing in which:

FIG. 2 represents an example of an initial reference model, FIG. 3 illustrates the processing performed to determine the occlusal plane, FIG. 4 (4a-4d) illustrates the step necessary for determining the tooth models in a reference model, FIG. 5 (5a-5d) illustrates the acquisition of updated images, and the trimming operation, FIG. 6 (6a-6b) illustrates the processing of an updated image making it possible to determine the outline of the teeth, FIG. 7 schematically illustrates the relative position of register marks 12 on updated images $14_1$ and $14_2$ of a separator 10, depending on the direction of observation (broken line)

DETAILED DESCRIPTION OF A METHOD FOR MONITORING THE POSITIONING OF THE TEETH

Figure 1:
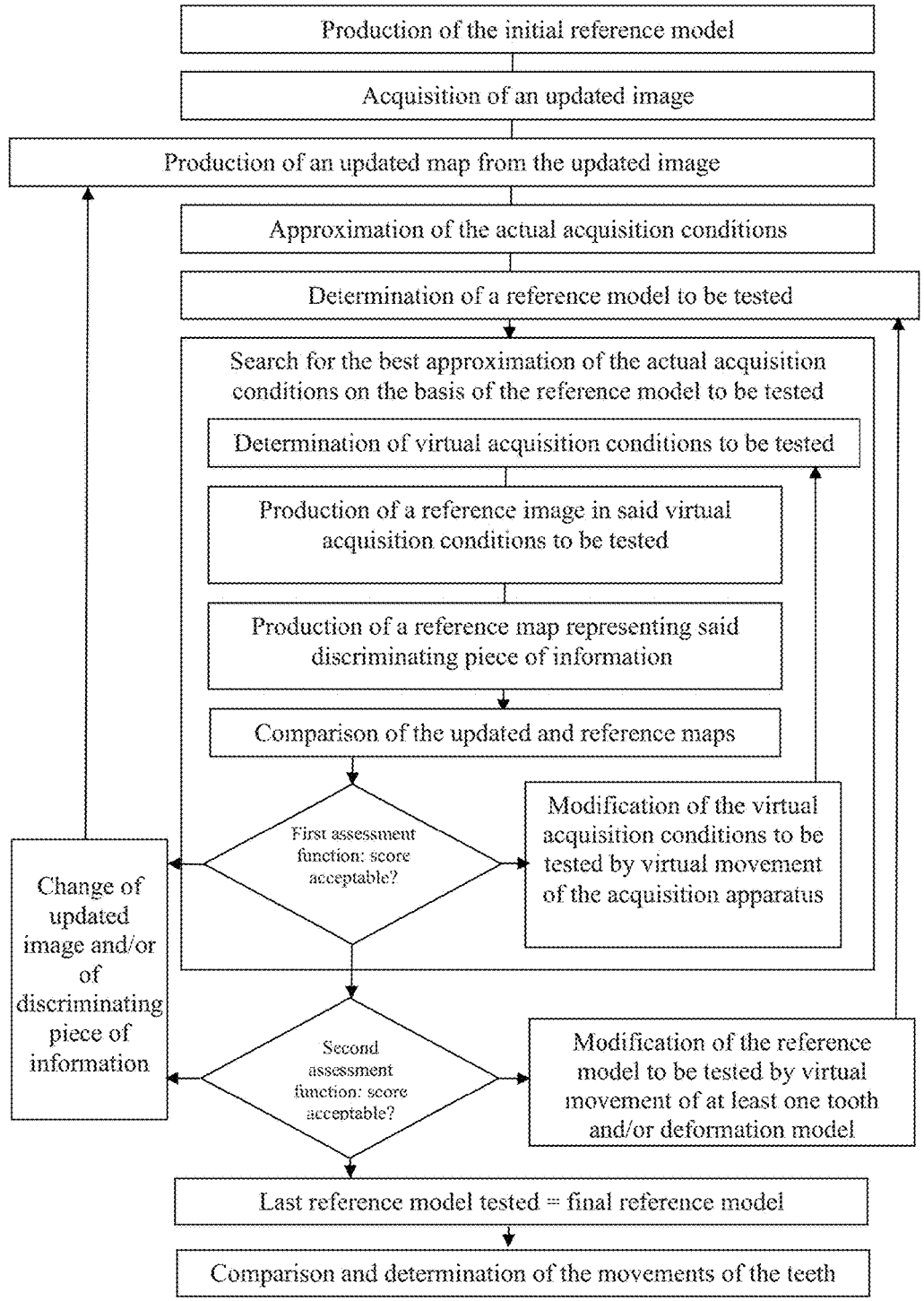
FIG. 1 represents a flow diagram illustrating the implementation of a method for monitoring the positioning and/or the shape of teeth according to the invention.

A method for monitoring the positioning of the teeth according to the invention comprises the steps mentioned above.

In the step a), an initial reference model of the arches, or of a part of the arches of the patient is created (see FIG. 2).

The initial reference model is a digital model in three dimensions of the arches of the patient, for example of .stl or .Obj, .DXF 3D, IGES, STEP, VDA, or point cloud type. Advantageously, such a model, called "3D" can be observed from any angle.

For the tracking of an orthodontic treatment, the initial reference model is preferably prepared at the start of the treatment. The initial reference model can correspond to a positioning of the teeth of the patient before the treatment or to a positioning of the teeth of the patient that the treatment sets out to achieve. In this case, the initial reference model is conventionally computed from a first three-dimensional model corresponding to the positioning of the teeth of the patient before the treatment.

To monitor for recurrence, the initial reference model is preferably prepared less than six months, preferably less than three months, even more preferably less than a month after the end of the orthodontic treatment, generally immediately after the end of the treatment. It thus corresponds to a substantially optimum positioning of the teeth.

The initial reference model can also be prepared independently of any treatment, for example because the patient wants to monitor the movements of his or her teeth.

The initial reference model can be prepared from measurements performed on the teeth of the patient or on a physical model of his or her teeth, for example a plaster model.

The initial reference model is preferably created by means of a professional apparatus, for example by means of a 3D scanner, preferably implemented by a health professional, for example by an orthodontist or an orthodontic laboratory. In an orthodontic practice, the patient or the physical model of his or her teeth can advantageously be arranged in a precise position and the professional apparatus can be refined. The result thereof is a very accurate initial reference model. The initial reference model preferably provides a piece of information on the positioning of the teeth with an error of less than $5/10$ mm, preferably less than $3/10$ mm, preferably less than $1/10$ mm.

Orientation of the Initial Reference Model:

Preferably, the orientation of the initial reference model in space, and in particular, preferably, the occlusal plane and the median longitudinal plane, are determined.

The occlusal plane and the median longitudinal plane can be determined manually, approximately. The inventors have however discovered methods that make it possible to determine these planes by computer processing.

Preferably, the reference model is a model of the arches with mouth closed, that is to say in a position in which teeth of the upper arch are in contact with teeth of the lower arch.

Conventionally, the initial reference model supplied by a three-dimensional scanner makes it possible to distinguish the upper arch from the lower arch. Generally, the model is supplied in the form of two files corresponding respectively to these arches, and comprising data making it possible to position the models of these arches relative to one another in the occlusal position.

Preferably, to estimate the points of contact between the teeth of the upper and lower arches, the set of the points of the model of the upper arch and of the lower arch which are at a distance less than a predetermined limit is determined, this limit preferably being less than 3 mm, preferably approximately 2 mm. All the other points of these models are then disregarded, which results in the representation of the upper right drawing of FIG. 3. A linear regression then makes it possible to determine the occlusal plane ("plane 1" in the lower left of FIG. 3).

The initial reference model can thus be oriented according to the occlusal plane (lower right drawing of FIG. 3).

If the initial reference model does not comprise data making it possible to position the upper and lower arches relative to one another, a check-bite is preferably used, revealing the points of contact between the upper teeth and the lower teeth, then the models of the upper and lower arches are repositioned in relation to this check-bite.

The median longitudinal plane is at right angles to the occlusal plane, but its orientation is unknown.

Preferably, the following procedure is applied to determine the orientation of the median longitudinal plane:

Axes [Ox) and [Oy) are considered in the occlusal plane, the point O being the barycenter of the normal projections of the points of contact on the occlusal plane.

In this reference frame (xOy), the curve, preferably parabolic, is sought which exhibits the greatest coefficient of correlation with the set of said projections.

The set of the projections of the points of contact is then moved in the occlusal plane, by rotation about the point O, and the preceding step is recommenced from this new angular position of the projections of the points of contact.

The cycle of the above operations is continued, preferably until the set of the points of contact has been rotated by 360° about the barycenter O. The coefficients of correlation corresponding to the different orientations of the set of the points of contact are then compared. The axis of the curve which leads to the highest coefficient of correlation is then considered as included in the median longitudinal plane, which makes it possible to precisely define the orientation thereof.

The orientation in space of the initial reference model is thus perfectly determined, rapidly.

Creation of the Tooth Models

In the initial reference model, a part which corresponds to a tooth, or "tooth model", is delimited by a gingival edge which can be broken down into an interior gingival edge (on the side of the interior of the mouth relative to the tooth), an exterior gingival edge (oriented toward the exterior of the mouth relative to the tooth) and two lateral gingival edges. The gingival edges correspond to regions in which the orientation of the surface defined by the initial reference model undergoes modifications of high amplitudes. These variations of orientation can be identified according to known techniques, for example by identifying the changes of direction of the normal to the surface modelled. FIG. 4a represents a view of the initial reference model processed to show these changes of direction. FIG. 4b shows the interior gingival edge which can be extracted by analysis of the image of FIG. 4a.

Figure 4C:

Several views of the initial reference model are thus analyzed, which makes it possible to determine the interior and exterior gingival edges in three dimensions, as represented in FIG. 4c.

Moreover, in projection in the occlusal plane, the interior and exterior gingival outlines of an arch approach one another on either side of a tooth. To determine a lateral gingival edge of a tooth, the shortest path is sought, on the surface of the initial reference model, between the two points of the interior and exterior gingival edges thus brought closer together and which substantially face one another. The search for the shortest path between two points on a three-dimensional model involves optimization techniques that are well known. Preferably, this search results from a metaheuristic method, preferably evolutionist, preferably from a simulated annealing.

Figure 4D:
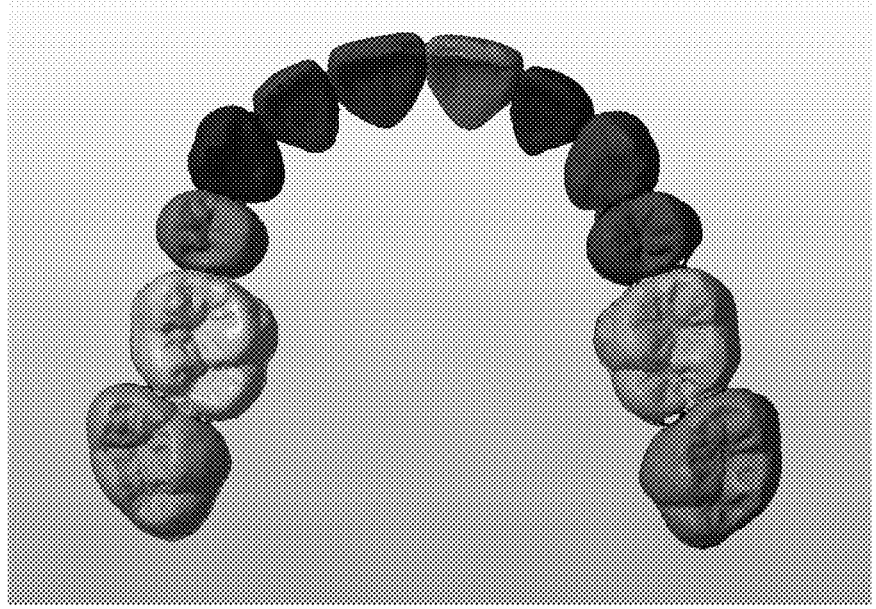

Two adjacent lateral gingival edges and the parts of the interior and exterior gingival edges which connect these lateral gingival edges thus make it possible to delimit a tooth at the gingival level. By taking account of the fact that a tooth extends from the gingival outline to the occlusal plane, it is thus possible to determine the parts of the initial reference model which correspond to the different teeth ("tooth models"). FIG. 4d represents the set of the tooth models of an arch.

The initial reference model can be stored in a centralized database, comprising the initial reference models of a plurality of patients. This database can be physically installed in a specialist establishment. It can also be installed in a laboratory or an orthodontic practice, which limits the transfers of confidential information.

In one embodiment, the initial reference model is handed to the patient. Preferably, a computer file corresponding to the initial reference model is stored on a removable medium, for example on a USB key or on an electronic card, preferably on a mobile phone, a tablet or a portable computer of the patient, and in particular on the personal appliance which will preferably be used in the steps b) and subsequent steps. Preferably, the patient or a dental health professional loads the initial reference model in said individual appliance or makes it available for loading in said individual appliance. The patient preferably loads the initial reference model from the Internet.

In a preferred embodiment, the reference model is not handed to the patient. Preferably, the reference model is only made available to a specialist establishment for implementing the steps c) to f). It can remain stored in the establishment in which it was produced in the step a) and where, preferably, the steps c) to f) are implemented.

In the step b), an updated image is taken of a part of an arch, of an arch or of the arches by means of an image acquisition apparatus. The step b) is preferably performed by the patient or one of his or her close relatives, but can be performed by a dentist.

Moment of Acquisition

Preferably, the updated image is taken after a time interval $\Delta t$ after the step a). The time interval $\Delta t$ can be predetermined. It can be constant, regardless of the occurrence of the method, that is to say that this interval relates to the first execution of the method or a subsequent execution. It can be variable, and depend for example on the results obtained following an earlier execution of the method. In particular, to monitor recurrence, the time interval $\Delta t$ can be even shorter when this execution has made it possible to detect a significant drift.

In a preferred embodiment, the time interval $\Delta t$ is determined by the orthodontist, according to a monitoring schedule. Based on the evolution of the position of the teeth, the orthodontist can modify this schedule and accordingly modify the time interval $\Delta t$. In one embodiment, the method for monitoring the position of the teeth according to the invention is executed several times, the time intervals between each execution being able to be identical or different. The time intervals between two successive executions can all be determined before the first execution to correspond to a monitoring schedule drawn up by the orthodontist.

The time interval $\Delta t$ can also be indeterminate and depend for example on decisions of the patient. For example, the creation of an updated image can be performed on the occasion of an appointment with the dentist or at any moment when the patient so wishes, even independently of any orthodontic treatment.

The time interval $\Delta t$ is preferably determined to correspond to a potentially significant evolution of the positioning of the teeth.

For example, to monitor recurrence, the time interval $\Delta t$ is preferably less than three months in the first year after the treatment. After this first year, the time interval $\Delta t$ is preferably greater than one month, even greater than six months or greater than twelve months. In particular, to detect a drift in the teeth, a time interval of between six months and eighteen months is suitable.

Preferably, at least one reminder informing the patient of the need to create an updated image is addressed to the patient. This reminder can be in paper form or, preferably, in electronic form, for example in the form of an email, an automatic alert from the specialist mobile application or an SMS. Such a reminder can be sent by the practice or the orthodontic laboratory or by the dentist or by the specialist mobile application of the patient, for example.

In a preferred embodiment, an updated image is acquired before the teeth have been able to move significantly, substantially at the same time as the creation of the initial reference model, preferably less than 7 days, less than 3 days, less than one day after the step a), that is to say before the teeth have been able to move significantly. The implementation of the method with this updated image advantageously makes it possible to check that the method does not lead to the detection of any difference between the initial and final reference models, and therefore that it is working correctly.

In one embodiment, the updated image can be acquired before the creation of the initial reference model. For example, the steps a) and b) can be performed at the end and at the start of an orthodontic treatment, respectively. It is thus notably possible to assess the effectiveness of the treatment in the absence of a 3D model at the start of treatment. The time interval $\Delta t'$ separating the steps a) and b) in this embodiment can notably take the values described above for $\Delta t$.

Image Acquisition Apparatus

Preferably, the image acquisition apparatus is a personal appliance commonly available in the market, for example a mobile phone, a so-called "connected" camera, a so-called "smart" watch, or a tablet or a personal computer, fixed or portable, comprising an image acquisition system, like a webcam or a camera, preferably a digital camera. Even though the updated image can in particular be created by a dentist, it is preferably created by the patient him or herself or by one of his or her near relatives.

In particular, the updated image can be crated by a person who has no particular knowledge of orthodontics, and in particular who has no degree in orthodontics or dentistry.

Preferably, the same acquisition apparatus is used to take all the updated images.

The image acquisition apparatus preferably weighs less than 3 kg, less than 2 kg, less than 1 kg, less than 500 g, preferably less than 300 g.

The step b) can therefore advantageously be performed at a distance from the step a), that is to say in a location different from that in which the step a) is performed, in particular at more than 50 m, more than 100 m, more than 1 km from the place where the step a) is performed, in particular outside of an orthodontic practice. In one embodiment, the step b) is not performed in a dental practice, an orthodontic practice or in an orthodontic laboratory, except, possibly, in a session intended to train the patient.

Preferably, the updated image is a photograph, in particular a panoramic photograph. In one embodiment, the updated image is extracted from a film.

In a preferred embodiment, the method uses several updated images to have at least one representation of each tooth, preferably at least three updated images corresponding to a front view, a right side view and a left side view of the teeth of the patient.

Preferably, in the step b), at least one updated image is taken in mouth closed position and at least one updated image is taken in mouth open position. The mouth closed image advantageously makes it possible to identify the relative movements between the two arches. The mouth open updated image advantageously makes it possible to clearly identify the outlines of the teeth, without the teeth of the upper arch concealing the teeth of the lower arch or vice versa.

The updated images can be taken either for the upper arch, or for the lower arch, or, preferably, for the two arches, all or part thereof.

Several similar images (representing substantially the same teeth) can also be useful in order to search for the best score. According to the acquisition conditions, a discriminating piece of information will in particular be able to lead to different results depending on the updated image used.

Figure 5A:
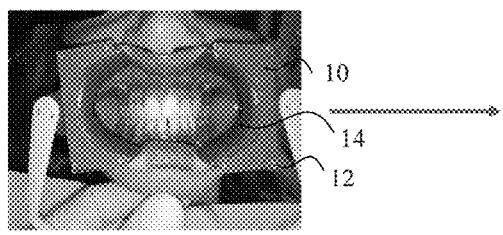
Figure 5B:
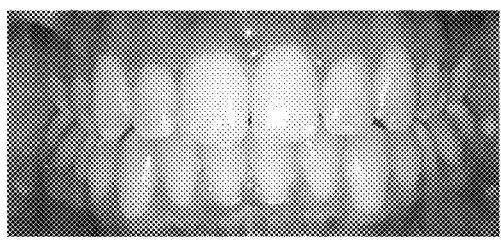
Figure 5C:
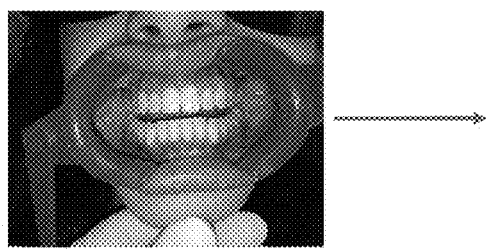
Figure 5D:
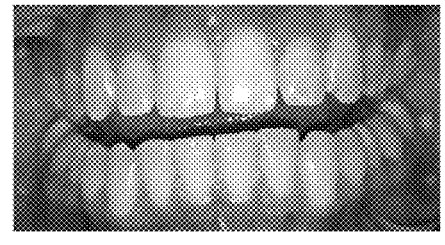

Preferably, a dental separator is used during the step b), as represented in FIGS. 5a and 5c. The first function of the separator is to separate the lips in order to improve the visibility of the teeth. Preferably, a separator is handed to the patient, for example at an appointment with his or her orthodontist or his or her dentist.

The image acquisition apparatus preferably supplies color images, and/or infrared images of the mouth of the patient, even of the face of the patient. The color images preferably represent the mouth of the patient with the actual colors of this mouth. The infrared images advantageously make it possible to show the teeth with an excellent contrast.

Preferably, the image acquisition apparatus comprises a specialist application making it possible to implement the step b), but also, preferably, the subsequent steps, preferably all the subsequent steps. Even more preferably, this application manages the reminders and informs the patient of the need to create an updated image.

Preferably, the specialist application is loaded into the image acquisition apparatus from a physical medium such as a USB key or a CD-ROM, or is downloaded over the Internet or wirelessly. In one embodiment, the specialist application is supplied to the patient by the practice and/or the orthodontic laboratory. It can in particular take the form of an application of the type of those commonly downloaded to iPhones of the Apple® brand or the appliances of all brands implementing the Android® operating systems or any other operating system.

The image acquisition apparatus preferably comprises a camera or a video or infrared camera, that the user, for example the patient or one of his or her close relatives, positions by means of a viewfinder or a screen, before actuating it.

Polarizing Means and Acquisition Kit

A method for monitoring the positioning of teeth according to the invention does not require an accurate positioning of the image acquisition apparatus relative to the teeth.

In one embodiment, no positioning constraint to ensure an arrangement of the image acquisition apparatus at less than 30 cm, less than 20 cm, less than 10 cm or less than 5 cm from a determined position is imposed.

Preferably, the image acquisition apparatus does however comprise polarizing means facilitating the approximate positioning thereof relative to the patient before the acquisition of the updated image.

The user can be guided by written and/or voice messages for the acquisition. For example, the personal appliance may announce "take a photo from the front", emit a signal to inform the user that the photo is acceptable or that, on the contrary, he or she must take another photo, announce "take a photo from the right", preferably by displaying an arrow to orient the user, etc. The end of the acquisition process can also be announced by the apparatus. The apparatus can also assist in the positioning, for example by visual messages (for example by displaying arrows), and/or audible messages (like a succession of beeps whose frequency increases as the positioning of the apparatus improves), and/or written and/or voice messages ("higher", "lower", etc.).

The polarizing means can in particular comprise references which appear on the viewfinder or the screen. The references can for example comprise a line intended to be aligned with the general direction of the join between the upper teeth and the lower teeth when the teeth are clamped by the patient, and/or a vertical line intended to be aligned with the join between the two upper incisors. The references can also refer to other parts of the patient. For example, they can consist of marks corresponding to the position of the eyes or take the form of an outline in which the mouth or the face of the patient must be positioned.

The reference or references are preferably "immobile" on the screen, that is to say that they do not move on the screen when the acquisition apparatus is moving.

In a preferred embodiment, the reference or references each correspond to a register mark borne by a reference frame added to the patient, that is to say that the patient did not have before the implementation of the method, preferably borne by a dental separator. A reference frame can also be a piece bitten on by the patient.

The register mark can have a surface area greater than 0.5 $mm^2$, preferably greater than 1 $mm^2$, preferably greater than 2 $mm^2$, preferably greater than 5 $mm^2$, preferably greater than 10 $mm^2$, even greater than 20 $mm^2$, even greater than 30 $mm^2$, and/or less than 50 $mm^2$.

Large dimensions conferred on a register mark or a proliferation of register marks advantageously make it possible to improve the accuracy of the positioning of the acquisition apparatus.

The register marks can be identical or different.

The register marks can notably be different according to their position, for example according to whether they are in the upper part or the lower part of the reference frame, and in particular of the separator, or to the right or to the left of the reference frame, and in particular the separator.

The register mark can be identical or different from the corresponding reference. It is preferably of geometrical shape, for example a dot, one or more lines, for example parallel, a star, a circle, an oval, a regular polygon, notably a square, a rectangle or a rhombus.

The register mark can also be an image, a letter, a digit or a sequence of letters and/or of digits.

The register mark is preferably of a different color from the surface of the separator which surrounds it, preferably so as to offer a high contrast.

A register mark can be visible or invisible to the naked eye, provided that it appears on the screen of the acquisition apparatus.

To improve the accuracy, the register marks are preferably separated from one another so that, when they correspond to their respective references on the screen, at least first and second register marks are less than 3 cm, preferably less than 2 cm, preferably less than 1 cm, preferably less than 0.5 cm, from first and second edges, respectively, of the screen. The first and second edges are preferably opposite edges of the screen.

The register mark can have one or more dimensions and/or a shape and/or a color that is/are identical or different from those of the corresponding reference.

The "correspondence" of a reference and of a register mark is a predefined arrangement relative to one another. It indicates a particular positioning of the acquisition apparatus relative to the register mark. The correspondence depends on the nature of the reference and on the register mark. The predefined situation, which corresponds to target acquisition conditions, can notably be a superimposition total or partial, a juxtaposition, or an alignment of the reference and of the register mark.

The exact superimposition of the reference and of the register mark makes it possible not only to determine the direction toward which the lens of the acquisition apparatus must point and/or the distance between the acquisition apparatus and the separator, but also, if the reference and/or the register mark are asymmetrical, the orientation of the acquisition apparatus around this direction.

The dimensions and/or the surface areas of a register mark and of the corresponding reference and/or the distance between several register marks and between the corresponding references can be used to set the distance between the acquisition apparatus and the arches.

The reference can for example be:
- a fixed line, on which the user must for example align register marks,
- a shape, preferably asymmetrical, corresponding to the shape of a register mark to be superimposed, for example a dot that the user must for example superimpose on the register mark, or a circle in which the user must for example place the register mark,
- a colored shape corresponding to the color of a register mark to be superimposed,
- a shape complementing the shape of a register mark, preferably so that the matching of the register mark and of the reference leads to a form having a direction, like a geometrical form, a letter or a text, a drawing, or a pattern, for example.

In a preferred embodiment, the references are defined, at least partially, from information supplied by the initial reference model. For example, according to the principles of "augmented reality", the reference can be a view of the initial reference model, for example a front view or a right side or a left side view of the initial reference model, made visible, transparent, on the screen of the image acquisition apparatus during the acquisition. It is thus very easy for the patient to approximately superimpose such a view with the teeth that he or she has to photograph.

In a preferred embodiment, the acquisition is performed by means of an acquisition kit according to the invention comprising:
- a dental separator, preferably made of a biocompatible material, comprising a register mark;
- an image acquisition apparatus, preferably of the type described above, comprising a screen for displaying a preview image, and a computer program comprising program code instructions for displaying at least one reference on said screen, said reference being preferably immobile on the screen, and arranged in a position called "position of match" in which, when the register mark matches the reference on the screen, the preview image represents the separator from a predetermined viewing angle and/or a predetermined distance.

A kit according to the invention advantageously allows for an acquisition of images without having recourse to a specialist person, notably an orthodontist. The acquisition of images can in particular be performed by the patient him or herself or by one of his or her close relatives, with a simple mobile phone, anywhere, and in particular outside of a medical, dental or orthodontic practice.

Furthermore, the image acquisition apparatus does not need to be mechanically stabilized, for example by means of a tripod or by incorporation in an apparatus placed on the ground.

Obviously, an acquisition kit does not allow a very accurate positioning of the acquisition apparatus relative to the teeth.

In particular, the accuracy of the positioning of the separator relative to the teeth is limited. The person who creates the images also positions the image acquisition apparatus approximately, despite the matching of the register mark relative to the reference on the screen. As will be seen in more detail hereinbelow in the description, the processing of the images does not however require a great accuracy of the positioning of the acquisition apparatus at the moment when the images are acquired.

Unlike the prior art, for example described in WO2006/065955, it is notably not necessary, at the moment of the acquisition of images, to use register marks whose positioning is perfectly defined relative to the teeth, particularly because they have been fixed on the teeth themselves or because they result from a local modification, at a precise point, of a tooth, for example by laser. The possibility of acquiring the images with a limited accuracy constitutes a considerable advantage, since it allows this acquisition at any location and by any person. The patient in particular no longer has a need to go to the orthodontist.

Preferably, no measurement of the teeth is performed to have the acquisition apparatus in the matching position.

Preferably, no register mark corresponding to a reference appearing on the screen is set directly on the teeth or on the gingiva or on a dental arch of the patient.

The acquisition apparatus can in particular be a mobile phone and the program can be a specialist application for mobile phones.

The separator can have the features of the separators used hitherto. It conventionally comprises a support provided with a rim extending around an aperture and arranged such that the lips of the patient can rest thereon leaving the teeth of the patient showing through said aperture (FIG. 5a and FIG. 5c).

The support, for example made of plastic, preferably has a substantially planar shape and a weight less than 500 g, preferably less than 300 g. The aperture is preferably formed substantially at the center of the support. The surface of the aperture is preferably greater than 15 cm$^2$, greater than 30 cm$^2$, greater than 40 cm$^2$, greater than 50 cm$^2$, and/or less than 100 cm$^2$, less than 80 cm$^2$, less than 60 cm$^2$.

Preferably, as represented in FIG. 5a, the separator comprises several register marks, preferably not aligned, preferably coplanar.

Preferably, the separator comprises at least three register marks and the computer program makes it possible to display on the screen of the acquisition apparatus one or more corresponding references.

In one embodiment, the positioning of the image acquisition apparatus results simply from the matching of references appearing on the screen of said acquisition apparatus with corresponding register marks, preferably with register marks of a dental separator.

In one embodiment, the reference or references which appear on the screen are determined according to the patient and/or the therapeutic treatment. In other words, the computer program is parameterized according to the patient in order for the images acquired to correspond specifically to the needs of the patient. Advantageously, at the moment of the acquisition of the images, the acquisition apparatus is therefore positioned in a substantially optimal position with respect to the particular features of the patient and/or the therapeutic treatment applied.

As will be seen in more detail hereinbelow in the description, the register marks of the separator preferably have a number of functions. First of all, they make it possible to guide the positioning of the image acquisition apparatus at the moment of the acquisition of the images, by means of corresponding references appearing on the screen of the acquisition apparatus. They also allow, in the step c), for a recropping of the updated images. Finally, the register marks of the separator, which appear on the images, make it possible, in the step d), to roughly determine virtual acquisition conditions approximating the actual acquisition conditions, which makes it possible to speed up the computer processing.

The steps c) and subsequent steps are preferably performed either on a personal appliance of the patient, preferably with the appliance used in the step b), or with an appliance of a dental health professional, or with a dedicated third party server.

In the step c), each updated image is analyzed so as to produce, for each updated image, an updated map relating to at least one discriminating piece of information.

Recropping

The analysis of the image can comprise a recropping of the updated image in order to isolate the relevant part, in particular to eliminate, at least partially, from the updated image, the elements which have not been the subject of the initial reference model, like the nose or the eyes of the patient or the separator. This recropping or "cropping", is facilitated by the representation of register marks on the updated image.

In particular, preferably, as represented in FIGS. 5a and 5c, the separator 10 bears at least three non-aligned register marks 12. If the separator is in several parts, for example conventionally in two parts, each part preferably bears at least three non-aligned register marks.

The shape of a register mark, for example an asymmetrical shape, can be also used to register the position of the separator on the updated image.

Preferably, the register marks have shapes and/or colors facilitating the identification thereof on a updated image. For example, they can be of black color while the rest of the separator is white.

In one embodiment, the register marks have shapes and/or colors making it possible to identify them individually. For example, they can each be of different color.

The identification of the register marks on the updated image makes it possible to identify the zone of the updated image containing the elements that have been the subject of the initial reference model, that is to say the teeth and the gingiva. The updated image can then be trimmed accordingly. The comparison of FIGS. 5a and 5b, or 5c and 5d, illustrates the effect of the recropping on an updated image.

Updated Map

Figure 6A:
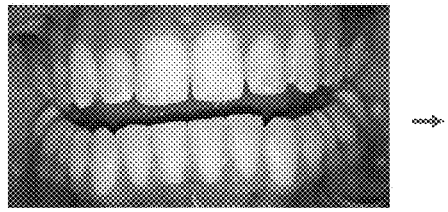
Figure 6B:
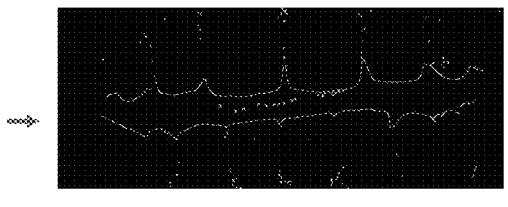

An updated map represents a discriminating piece of information in the reference frame of the updated image. For example, FIG. 6b is an updated map relating to the outline of the teeth obtained from the updated image of FIG. 6a.

The discriminating information is preferably chosen from the group consisting of a piece of outline information, a piece of color information, a piece of density information, a piece of distance information, a piece of brightness information, a piece of saturation information, a piece of information on the glare and combinations of such pieces of information.

A person skilled in the art knows how to process an updated image to show the discriminating information. This processing comprises, for example, the application of masks or filters that are well known, supplied with the image processing software. Such processing operations make it possible, for example, to detect the regions of strong contrast to determine outlines.

These processing operations notably comprise one or more of the following known and preferred methods, namely:

by application of a Canny filter, notably to search for the outlines by using the Canny algorithm;

by application of a Sobel filter, notably to compute drifts by means of the extended Sobel operator;

by application of a Laplace filter, to compute the laplacien of an image;

by spot detection on an image ("Blobdetector");

by application of a threshold ("Threshold") to apply a set threshold to each element of a vector;

by resizing, by using relationships between the areas of pixels ("Resize(Area)") or bi-cubic interpolations on the environment of the pixels;

by erosion of the image by means of a specific structuring element;

by expansion of the image by means of a specific structuring element;

by touching up, in particular by using regions in the vicinity of the restored zone;

by application of a bilateral filter;

by application of a Gaussian blur;

by application of an Otsu filter, to search for the threshold which minimizes the intraclass variants;

by application of an A* filter, to search for a path between points;

by application of an adaptive threshold ("Adaptive Threshold") to apply an adaptive threshold to a vector;

by application of an equalization filter of a histogram of an image in shades of grey in particular;

by blur detection ("BlurDetection"), to compute the entropy of an image by using its laplacien;

by detection of outlines ("FindContour") of a binary image;

by color filling ("FloodFill"), notably to fill a connected element with a determined color.

The following nonlimiting methods, although they are not preferred, can also be implemented:

by application of a "MeanShift" filter, so as to find an object on a projection of the image;

by application of a "CLAHE" filter, which stands for "Contrast Limited Adaptive Histogram Equalization";

by application of a "Kmeans" filter, to determine the center of clusters and of groups of samples around clusters;

by application of a DFT filter, so as to perform a discrete Fourier transformation, direct or inverse, of a vector;

by computation of moments;

by application of a "HuMoments" filter, for computing invariants of Hu invariants;

by computation of the integral of an image, by application of a Scharr filter, making it possible to compute a drift of the image by implementing a Scharr operator;

by searching for the point convex envelope ("ConvexHull");

by searching for points of convexity of an outline ("ConvexityDefects");

by shape comparison ("MatchShapes");

by verification of whether points are within an outline ("PointPolygonTest"); by detection of Harris outlines ("CornerHarris");

by searching for minimum eigenvalues of gradient matrices, to detect corners ("CornerMinEigenVal");

by application of a Hough transform to find circles in an image in shades of grey ("HoughCircles");

by "Active contour modeling" (plotting the outline of an object from a potentially "noisy" 2D image);

by computation of a force field, called GVF ("gradient vector flow"), in a part of the image;

by cascade classification ("CascadeClassification");

by "Deepleraning".

Preferably, the discriminating information is optimized by means of an optimization method according to the invention comprising steps C1 to C3.

In the optional step d), actual acquisition conditions during the step b) are roughly determined. In other words, at least the relative position of the image acquisition apparatus at the moment when the updated image was taken (position of the acquisition apparatus in space and orientation of this apparatus) is determined. The step d) advantageously makes it possible to limit the number of tests on virtual acquisition conditions during the step e), and therefore makes it possible to considerably speed up the step e).

One or more heuristic rules are preferably used. For example, preferably, there are excluded, from the virtual acquisition conditions likely to be tested in the step e), the conditions which correspond to a position of the image acquisition apparatus behind the teeth or at a distance from the teeth greater than 1 m.

Figure 7:
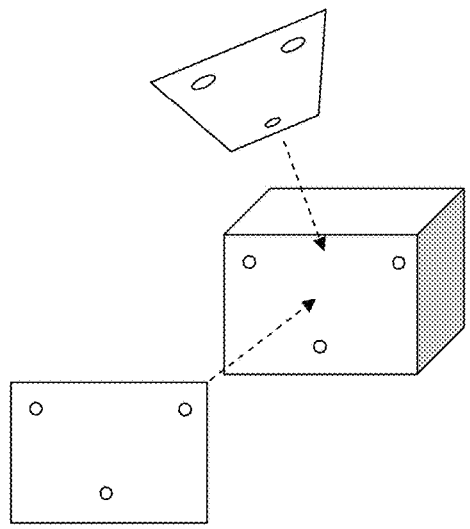

In a preferred embodiment, as illustrated in FIG. 7, register marks are used that are represented on the updated image, and in particular register marks 12 of the separator, to determine a substantially conical region of space delimiting the virtual acquisition conditions likely to be tested in the step e), or "test cone".

Specifically, there are preferably at least three non-aligned register marks 12 on the separator 10, for example, and their relative positions are measured accurately on the separator.

The register marks are then identified on the updated image, as described previously. Simple trigonometrical computations make it possible to approximately determine the direction from which the updated image has been taken. A cone oriented in this direction, the vertex of which is at the level of the separator and the half angle of which at the vertex is preferably less than 10°, preferably less than 5°, for example 3°, can then be defined as "test cone". The half-angle at the vertex corresponds to a degree of uncertainty. The smaller the half-angle at the vertex, the greater the probability that the virtual acquisition conditions corresponding to the actual acquisition conditions are outside of the test cone.

For example, when the updated image is taken at right angles to the plane of the three register marks on the separator, it can be deduced therefrom that the acquisition apparatus was substantially within a test cone whose axis is substantially at right angles to this plane during the taking of the updated image. If the relative positions of the three register marks on the updated image are different from those that the register marks occupy on the separator, the axis of the test cone within which the search for the positioning of the acquisition apparatus during the acquisition of the updated image is limited is inclined relative to the plane of the register marks, as represented in FIG. 7.

In a particular embodiment, as illustrated in FIGS. 5a and 5c, the separator comprises independent left and right parts, which each comprise at least three register marks, preferably at least four register marks. A left test cone can thus be determined by means of the register marks of the left-hand part and a right test cone can be determined by means of the register marks of the right-hand part of the separator. The virtual acquisition conditions likely to be tested can then be limited to positions of the acquisition apparatus in space belonging to these two test cones. It is also possible to consider that the best assessment of the position of the acquisition apparatus corresponds to the mean position between the best position in the left test cone and the best position in the right search cone.

The position of the register marks on the updated image also makes it possible to assess the trim of the acquisition apparatus during the capture of the updated image. For example, if it is known that two register marks are substantially aligned in a horizontal direction during the acquisition of the updated image, the direction of the straight line containing these two points on the updated image provides an indication on the orientation of the acquisition apparatus in the actual acquisition conditions.

Finally, the size and the surface area of the register marks on the updated image or their spacing can make it possible to assess the distance between the image acquisition apparatus and the teeth during the acquisition of the updated image, and therefore to reduce the test cone to a truncated cone.

In the optional step d), it is also possible to use data supplied by the acquisition apparatus and concerning its orientation, for example gyroscopic data.

Preferably, in the step d), the calibration of the actual acquisition apparatus during the step b) is roughly determined.

The way in which each calibration parameter acts on the acquired image is well known. In particular, the operation of an acquisition apparatus can be conventionally modelled so as to be able to test a particular calibration on the acquired image. The inventors have inverted such a model, within no particular technical difficulty, in order, through the analysis of the representation of the separator, for it to be possible to roughly assess the calibration of the acquisition apparatus during the step b).

For example, the ratio between the surface area of the register marks on the updated image and the surface area of the updated image makes it possible to assess the focal distance of the acquisition apparatus during the step b). The representation of a register mark whose optical characteristics are known make it possible to assess the exposure time and the sensitivity.

In a preferred embodiment, a register mark is a relief which does not extend exclusively in the general plane of the separator, corresponding to a plane parallel to the frontal (or coronal) plane. Preferably, a register mark is a relief which extends in a plane substantially at right angles to the general plane of the separator. The relief can in particular take the form of a tongue which, when the separator is in its service position, extends toward the bottom of the mouth.

The analysis of the representation of this relief advantageously makes it possible to assess the depth of field. Alternatively, two register marks which are not in a same frontal plane can be used for this purpose.

The step d) allows only a rough assessment of the actual acquisition conditions. The step d) does however make it possible to determine a restricted set of virtual acquisition conditions likely to correspond to the actual acquisition conditions, and, in this set, virtual acquisition conditions constituting the best point of departure for the step e1) described hereinbelow.

The step d) also makes it possible to detect updated images unsuitable for continuing the method, for example an updated image which does not show the register marks. Preferably, the method is then restarted at the step c) with a new updated image.

Obviously, the different methods that can be implemented in the step d) can be combined.

The objective of the step e) is to modify the initial reference model to obtain a final reference model which corresponds to the updated image. Ideally, the final reference model is therefore a three-dimensional digital reference model from which the updated image could have been taken if this model had been real.

A succession of reference models "to be tested" is therefore tested, the choice of a reference model to be tested being preferably dependent on the level of match of the reference models "to be tested" previously tested with the updated image. This choice is preferably made according to a known optimization method, in particular chosen from the metaheuristic optimization methods, preferably evolutionist, in particular the simulated annealing methods.

In the step e1), it is determined that the reference model to be tested is the initial reference model during the first execution of the step e2).

In the step e2), the first step is to determine virtual acquisition conditions to be tested, that is to say a virtual position and a virtual orientation likely to match the actual position and orientation of the acquisition apparatus during the capture of the updated image, but also, preferably, a virtual calibration likely to match the actual calibration of the acquisition apparatus during the capture of the updated image.

The first virtual acquisition conditions to be tested can be random. Preferably, they are chosen from the limited set determined in the step d), and even more preferably, correspond to virtual acquisition conditions corresponding, according to the step d), to the most promising virtual acquisition conditions, that is to say those constituting the best springboard for approximating, as rapidly as possible, the actual acquisition conditions (step e21)).

The image acquisition apparatus is then virtually configured in the virtual acquisition conditions to be tested in order to acquire a reference image of the reference model in these virtual acquisition conditions to be tested. The reference image therefore corresponds to the image that the image acquisition apparatus would have taken if it had been placed, relative to the reference model to be tested, and optionally calibrated in the virtual acquisition conditions to be tested (step e22)).

If the updated image was taken at the same moment that the reference model was produced, and if the virtual acquisition conditions are exactly the actual acquisition conditions, the reference image can therefore be exactly superimposed on the updated image. The differences between the updated image and the reference image result from errors in the assessment of the virtual acquisition conditions (if they do not correspond exactly to the actual acquisition conditions) and from movements of the teeth between the step b) and the reference model to be tested.

To compare the updated and reference images, the discriminating information is compared on these two images. More specifically, from the reference image, a reference map is produced representing the discriminating information (step e23)).

The updated and reference maps, the two of them relating to the same discriminating information, are then compared and the difference between these two maps is assessed by means of a score. For example, if the discriminating information is the outline of the teeth, it is possible to compare the mean distance between the points of the outline of the teeth which appears on the reference image and the points of the corresponding outline which appears on the updated image, the score being all the higher as this distance shortens.

Preferably, the virtual acquisition conditions comprise the calibration parameters of the acquisition apparatus. The score is all the higher as the values of the calibration parameters tested come closer to the values of the calibration parameters of the acquisition apparatus used in the step b). For example, if the diaphragm aperture tested is far from that of the acquisition apparatus used in the step b), the reference image exhibits blurred regions and sharp regions which do not correspond to the blurred regions and to the sharp regions of the updated image. If the discriminating information is the outline of the teeth, the updated and reference maps do not therefore represent the same outlines and the score will be low.

The score can for example be a coefficient of correlation.

The score is then assessed by means of a first assessment function. The first assessment function makes it possible to decide whether the cycling on the step e2) must be continued or stopped. The first assessment function can for example be equal to 0 if the cycling must be stopped or be equal to 1 if the cycling must continue.

The value of the first assessment function can depend on the score reached. For example, it may be decided to continue the cycling on the step e2) if the score does not exceed a first threshold. For example, if an exact match between the updated and reference images leads to a score of 100%, the first threshold can be, for example, 95%. Obviously, the higher the first threshold, the better the accuracy of the assessment of the virtual acquisition conditions if the score comes to exceed this first threshold.

The value of the first assessment function can also depend on scores obtained with virtual acquisition conditions tested previously.

The value of the first assessment function can also depend on random parameters and/or on the number of cycles of the step e2) already performed.

In particular, it is possible, despite the repetition of the cycles, not to manage to find virtual acquisition conditions which are sufficiently close to the actual acquisition conditions for the score to reach said first threshold. The first assessment function may then lead to the decision to quit the cycling although the best score obtained has not reached said first threshold. This decision may result, for example, from a number of cycles greater than a predetermined maximum number.

A random parameter in the first assessment function can also authorize the continuation of tests of new virtual acquisition conditions, although the score appears satisfactory.

The assessment functions conventionally used in the metaheuristic, preferably evolutionist, optimization methods, particularly in the simulated annealing methods, can be used for the second assessment function.

If the value of the first assessment function indicates that it is decided to continue the cycling in the step e2), the virtual acquisition conditions tested (step e25)) are modified and a cycle (step e2)) is recommenced consisting in producing a reference image and a reference map, then in comparing this reference map with the updated map to determine a score.

The modification of the virtual acquisition conditions corresponds to a virtual movement in space and/or to a modification of the orientation and/or, preferably, to a modification of the calibration of the acquisition apparatus. This modification can be random, provided however that the new virtual acquisition conditions to be tested still belong to the set determined in the step d). The modification is preferably guided by heuristic rules, for example by favoring the modifications which, according to an analysis of the preceding scores obtained, appear the most favorable to increase the score.

Figure 12A:
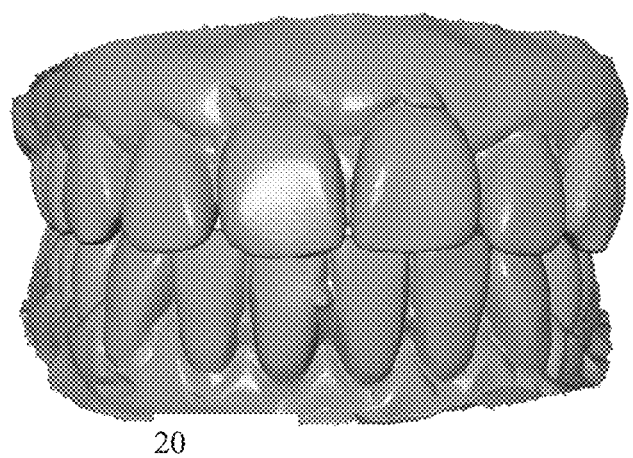
FIGS. 12a and 12b illustrate two views of a three-dimensional model with two different focal distances.
Figure 12B:
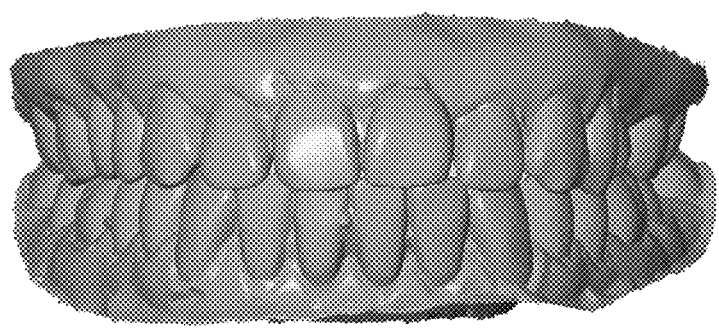

FIGS. 12a and 12b illustrate for example the effect of a modification of the virtual acquisition conditions, in this case of a modification of the focal distance, on the reference image.

The cycling on e2) is continued until the value of the first assessment function indicates that it is decided to exit from this cycling and to continue to the step e3), for example if the score reaches or exceeds said first threshold.

The optimization of the virtual acquisition conditions in the step e2) is preferably performed by using a metaheuristic method, preferably evolutionist, preferably a simulated annealing algorithm. Such an algorithm is well known for nonlinear optimization.

If the cycling was left on the step e2), without a satisfactory score having been able to be obtained, for example without the score having been able to reach said first threshold, the method can be stopped (failure situation) or restarted at the step c) with a new discriminating piece of information and/or with a new updated image. The method can also be continued with the virtual acquisition conditions corresponding to the best score reached. A warning can be emitted in order to inform the user of the error on the result.

If the cycling was left on the step e2) although a satisfactory score was able to be obtained, for example because the score reached, even exceeded, said first threshold, the virtual acquisition conditions correspond substantially to the actual acquisition conditions.

Preferably, the virtual acquisition conditions comprise the calibration parameters of the acquisition apparatus. The method conducted thus makes it possible to assess the values of these parameters without it being necessary to know the nature of the acquisition apparatus or its setting. The step b) can therefore be performed with no particular precautions, for example by the patient him or herself by means of his or her mobile phone.

Furthermore, the search for the actual calibration is performed by comparing an updated image with views of an initial reference model in virtual acquisition conditions that are tested. Advantageously, it does not require the updated image to show a standard calibration gauge, that is to say a gauge whose features are precisely known making it possible to determine the calibration of the acquisition apparatus.

WO2006/065955, incorporated for reference, describes the use of images to build three-dimensional models in the field of orthodontic treatments. However, this document does not describe the method that makes it possible to use simple photographs, conventionally presenting partial images of the teeth, blurred image portions and variable glares, taken generally nonsimultaneously, without needing to select noteworthy points on the images, and with an acquisition apparatus whose calibration is unknown.

In a method for monitoring the positioning of teeth according to the invention, the updated images are not used to create a totally new updated three-dimensional model, but only to modify the initial, very accurate, reference model. A totally new updated three-dimensional model created from simple photographs taken with no particular precautions would in particular be too inaccurate for a comparison with the initial reference model to be able to lead to conclusions on the movement of the teeth.

Differences may remain between the virtual acquisition conditions determined and the actual acquisition conditions, particularly if teeth have moved between the steps a) and b). The correlation between the updated and reference images can then be further enhanced by repeating the step e2), the reference model to be tested then being modified by movement of one or more tooth models (step e3)).

The search for the reference model best approximating the positioning of the teeth during the acquisition of the updated image can be performed like the search for the virtual acquisition conditions best approximating the actual acquisition conditions (step e2)).

In particular, the score is assessed by means of a second assessment function. The second assessment function makes it possible to decide whether the cycling on the steps e2) and e3) must be continued or stopped. The second assessment function can for example be equal to 0 if the cycling must be stopped or be equal to 1 if the cycling must continue.

The value of the second assessment function depends preferably on the best score obtained with the reference model to be tested, that is to say on the differences between the updated and reference maps, in the virtual acquisition conditions best approximating said actual acquisition conditions.

The value of the second assessment function can also depend on the best score obtained with one or more reference models tested previously.

For example, it may be decided to continue the cycling if the score does not exceed a second minimum threshold. The value of the second assessment function can also depend on random parameters and/or on the number of cycles of the steps e2) and e3) already performed.

The assessment functions conventionally used in the metaheuristic optimization methods, preferably evolutionist, particularly in the simulated annealing methods, can be used for the second assessment function.

If the value of the second assessment function indicates that it is decided to continue the cycling on the steps e2) and e3), the reference model to be tested is modified and a cycle (steps e2) and e3)) is recommenced with the new reference model to be tested.

The modification of the reference model to be tested corresponds to a movement of one or more tooth models. This modification can be random. The modification is preferably guided by heuristic rules, for example by favoring the modifications which, according to an analysis of the preceding scores obtained, appear most favorable for increasing the score.

Preferably, the movement of a tooth model is sought which has the greatest impact on the score, the reference model to be tested is modified by moving this tooth model, then the cycling is continued on the steps e2) and e3) so as to optimize the score. It is then possible to search, among the other tooth models, for the one which has the greatest impact on the improvement of the score, and once again search for the optimum movement of this other tooth model on the score. This approach can thus be continued with each tooth model.

Next, it is possible to repeat a cycle over the set of the tooth models and to continue thus until a score is obtained that is above the second threshold. Obviously, other strategies can be used to move one or more tooth models in the reference model to be tested and search for the maximum score.

The cycling on the steps e2) and e3) is continued until the value of the second assessment function indicates that it is decided to exit from this cycling and to continue at the step f), for example if the score reaches or exceeds said second threshold.

The search for a reference model with a cycling on the steps e2) and e3) to search for the positions of the tooth models which optimize the score is preferably performed by using a metaheuristic method, preferably evolutionist, preferably a simulated annealing algorithm. Such an algorithm is well known for nonlinear optimization.

If the cycling on the steps e2) and e3) was left without a satisfactory score having been able to be obtained, for example without the score having been able to reach said second threshold, the method can be stopped (failure situation) or restarted at the step c) with a new discriminating piece of information and/or with a new updated image.

If it is decided to restart the method at the step c) from another discriminating piece of information and/or another updated image because the first threshold or the second threshold has not been reached, the choice of the new discriminating information and/or of the new updated image can depend on the scores obtained previously, in order to favor the discriminating information and/or the updated image which, in light of these scores, appear the most promising.

A new discriminating piece of information, obtained for example by the combination of other discriminating pieces of information already tested, can be used. If necessary, there may also be prompting to acquire one or more new updated images. Preferably, indications are provided that make it possible to guide the positioning of the acquisition apparatus for the capture of this new updated image. For example, it is possible to indicate to the patient that he or she should take a photo from the right part of his or her lower arch.

If the cycling on the steps e2) and e3) was left without a satisfactory score having been able to be obtained, the method can also be continued with the reference model and the virtual acquisition conditions corresponding to the best score reached. A warning can be emitted in order to inform the user of the error on the result.

If the cycling on the steps e2) and e3) was left when the satisfactory score was able to obtained, for example because the score reached, even exceeded, said second threshold, the virtual acquisition conditions correspond substantially to the actual acquisition conditions and the tooth models in the reference model obtained (called "final reference model") are substantially in the position of the teeth of the patient at the moment of the step b).

The cycling on the steps e2) and e3) advantageously makes it possible to improve the assessment of the calibration parameters of the acquisition apparatus in the step b).

In the step f), the final reference model, resulting from the optimization by movement of the tooth models, is compared with the initial reference model. The final reference model corresponds substantially to the updated image. The comparison of the step f) therefore makes it possible to observe the differences between the positioning of the teeth in the step a) (initial reference model) and during the acquisition of the updated image (step b)). The method thus makes it possible to determine accurately, for each of the teeth, the movements between these two steps.

By repeating the steps b) and subsequent steps, it is also possible to assess the rate of change of the position of the teeth, and thus to measure, for example, the effectiveness of an orthodontic treatment. A method for monitoring the positioning of teeth according to the invention can for example be used to remotely track the evolution of an orthodontic treatment, and thus to minimize the appointments of the patients with their orthodontists.

In a preferred embodiment, the monitoring method according to the invention is implemented several times for a same patient, preferably successively with several discriminating pieces of information, preferably more than 2, more than 3, more than 5 discriminating pieces of information for each updated image and/or with several updated images, preferably more than 2, more than 3, more than 5 updated images. The assessment of the movement of a tooth can thus be refined by taking account of the different scores obtained. The comparison of these scores also makes it possible, if appropriate, to discard the unsatisfactory discriminating pieces of information and/or updated images.

Based on the movement measured, a practical information can be generated. If the movement is small, this practical information can be that no action is to be undertaken. On the other hand, if one or more teeth have moved substantially, the information can be to schedule a visit to the dentist or the orthodontist. Preferably, the practical information depends on the degree of movement of the teeth. In one embodiment, an appointment can be automatically taken with the dentist or the orthodontist, according to the amplitude and/or the nature of the movements detected.

In one embodiment, the practical information is used to modify the time interval after which the patient will have to be alerted that a new updated image must be created.

In one embodiment, the individual apparatus makes it possible to display images, even a sequence of images, showing the positioning of the teeth on different dates. These images can be presented in the form of an animation, for example in the form of a slide show or of a film.

Preferably, the image acquisition apparatus is a telephone which makes it possible to transmit the results obtained by the implementation of the method, preferably securely.

The communication can for example be made, at least partly, wirelessly, preferably according to at least one protocol chosen from the edge, 3G, 4G, udmsa, hpdmsa, Bluetooth and Wi-Fi protocols, or by any other protocol, suited to mobile or roaming equipment items, by wired synchronisation with the personal computer, or by optical transmission.

As now emerges, a method for monitoring the positioning of the teeth according to the invention allows for an accurate and effective monitoring of the positioning of the teeth of the patient, substantially without stress for the patient. In particular, simple photographs taken with no particular precaution, for example with a mobile phone, are sufficient. The patient can therefore easily implement this method.

Detailed Description of a Method for Monitoring the Shape of the Teeth

The invention relates also to a method for monitoring the shape of teeth of a patient. In the step a), the definition of the tooth models is not however essential for this monitoring. Preferably, in the step e), for each updated image, a final reference model is sought that corresponds to the shape of the teeth during the acquisition of the updated image, the search being preferably performed by means of a metaheuristic method, preferably evolutionist, preferably by simulated annealing, in particular by means of one of the metaheuristic methods described previously.

Preferably, as described for the step e), this search comprises two interleaved optimization loops.

During the first optimization operation, in a reference model to be tested which is initially the initial reference model, virtual acquisition conditions which best correspond to the actual acquisition conditions are first of all optimized. In particular, the virtual position of the acquisition apparatus relative to the reference model to be tested which offers the view of this reference model to be tested, that is to say the reference image, which is closest to the updated image, is sought.

Preferably, as described previously, a virtual calibration is also sought that is likely to correspond to the actual calibration of the acquisition apparatus during the capture of the updated image.

During the second optimization operation, the reference model to be tested is then modified, the first optimization operation is repeated, then these two operations are recommenced until the reference model to be tested and the virtual position of the acquisition apparatus which make it possible to obtain the reference image which is closest to the updated image is found.

These operations are similar to those described for the method for monitoring the positioning of the teeth and the optional features of the latter monitoring are optionally applicable.

However, according to the method for monitoring the positioning of the teeth described previously, the modification of the reference model results from a movement of one or more tooth models. No deformation of the tooth models or of the initial reference model is necessary.

To monitor the shape of the teeth, the modification of the reference model results from a modification of the shape of the reference model to be tested, in particular of one or more tooth models. No movement of the tooth models is necessary.

Obviously, it is preferable to perform both types of modifications of the reference model to be tested in order to determine a final reference model which takes account both of the movement of the teeth and of their deformation.

For example, a third optimization operation can be implemented relating to the movement of the teeth and bracketing the two first optimization operations, the second optimization relating to the shape of the tooth models or of the reference model to be tested. It is also possible to implement only the two first optimization operations, by modifying, possibly simultaneously, the shape and the position of the tooth models during the second optimization operation.

It is also possible to implement a third optimization operation relating to the shape of the tooth models or of the reference model to be tested and bracketing the two first optimization operations, the second optimization operation relating to the movement of the tooth models. For example, a final reference model "to be tested" is first of all sought that best takes account of movement of the tooth models, the final reference model to be tested corresponding to the final reference model of a step e) of a method for monitoring the positioning of the teeth described previously, then there is a search to see if a deformation of the final reference model to be tested can lead to a better match with the updated image. For this search, the final reference model to be tested is deformed, the first two optimization operations are recommenced, then, based on the match obtained, the search is stopped or it is continued by performing a new deformation of the final reference model to be tested and by repeating an execution of the first two optimization operations.

Preferably, the first optimization operation and/or the second optimization operation and/or the third optimization operation, preferably the first optimization operation and the second optimization operation and the third optimization operation implement a metaheuristic method, preferably evolutionist, preferably a simulated annealing, in particular one of the metaheuristic methods cited previously.

Preferably, to monitor the deformation of the teeth, the step e) comprises
 a first optimization operation making it possible to search for the virtual acquisition conditions that best correspond to the actual acquisition conditions in a reference model to be tested determined from the initial reference model, and
 a second optimization operation making it possible to search, by testing a plurality of said reference models to be tested, for the reference model that best corresponds to the shape of the teeth of the patient during the acquisition of the updated image in the step b), preferably that best corresponds to the shape and to the positioning of the teeth of the patient during the acquisition of the updated image in the step b).

Preferably, a first optimization operation is performed for each test of a reference model to be tested during the second optimization operation.

The step e) can notably comprise the following steps:
 e'1) definition of the reference model to be tested as being the initial reference model then,
 e'2) according to the following steps, testing of virtual acquisition conditions with the reference model to be tested in order to finely approximate said actual acquisition conditions;
  e'21) determination of virtual acquisition conditions to be tested;
  e'22) production of a two-dimensional reference image of the reference model to be tested in said virtual acquisition conditions to be tested;
  e'23) processing of the reference image to produce at least one reference map representing said discriminating piece of information;
  e'24) comparison of the updated and reference maps so as to determine a value for a first assessment function, said value for the first assessment function depending on the differences between said updated and reference maps and corresponding to a decision to continue or to stop the search for virtual acquisition conditions approximating said actual acquisition conditions with greater accuracy than said virtual acquisition conditions to be tested determined on the last occurrence of the step e'21);
  e'25) if said value for the first assessment function corresponds to a decision to continue said search, return to the step e'21) by modifying the virtual acquisition conditions to be tested;
 e'3) otherwise, determination of a value for a second assessment function, said value for the second assessment function depending on the differences between the updated and reference maps in the virtual acquisition conditions best approximating said actual acquisition conditions and resulting from the last occurrence of the step e'2), said value for the second assessment function corresponding to a decision to continue or to stop the search for a reference model approximating the shape, and possibly the positioning, of the teeth during the acquisition of the updated image with greater accuracy than said reference model to be tested used on the last occurrence of the step e'2), and
  if said value for the second assessment function corresponds to a decision to continue said search, modification of the reference model to be tested by deformation of one or more tooth models, or of the reference model to be tested, and possibly by movement of one or more tooth models, then return to the step e'2).

The completion of this method culminates in a reference model to be tested, called "final reference model", which corresponds to the deformed initial reference model to best correspond to the updated image.

The comparison of the initial and updated reference models comprises the comparison of the spatial coordinates of the points of the surfaces defined by these two reference models. It is thus possible to deduce therefrom any modifications of shape between the step a) and the step b).

Figure 8:
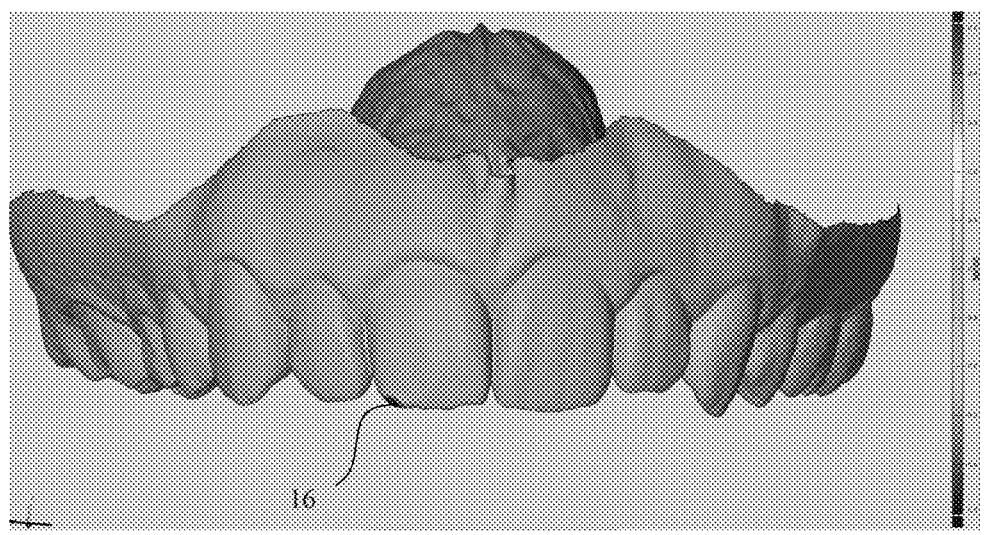
FIG. 8 represents a mapping resulting from the implementation of a method for monitoring the shape of teeth of a patient according to the invention.

Preferably, a mapping of the tooth is produced showing the changes of shape. Preferably, as represented in FIG. 8, the color of a zone of the mapping is a function of the scale of change of shape of this zone. The mapping of FIG. 8 shows in particular a zone 16 indicating a break of a tooth.

Obviously, the method for monitoring the shape of teeth of a patient can be used to detect an addition or a subtraction of material, but also a deformation with constant volume. This method also makes it possible to detect movements of teeth, even without a tooth model. However, in the absence of a tooth model, it does not make it possible to distinguish the deformations of the teeth on the one hand and the movements of the teeth on the other hand.

Detailed Description of a Method for Monitoring the Appearance of the Teeth

The monitoring of the changing of color of teeth from photographs taken in positions of the camera or in different light environments shows that this comparison does not make it possible to assess a change in the appearance of these teeth.

Such monitoring of the color of the teeth therefore requires particular precautions, notably to accurately define the position of the camera and its light environment.

There is therefore a need for a method that makes it possible to monitor the color, and more generally a property of appearance, of the teeth that is simpler, and notably by avoiding these particular precautions.

One aim of the invention is to address this need.

Figure 9:
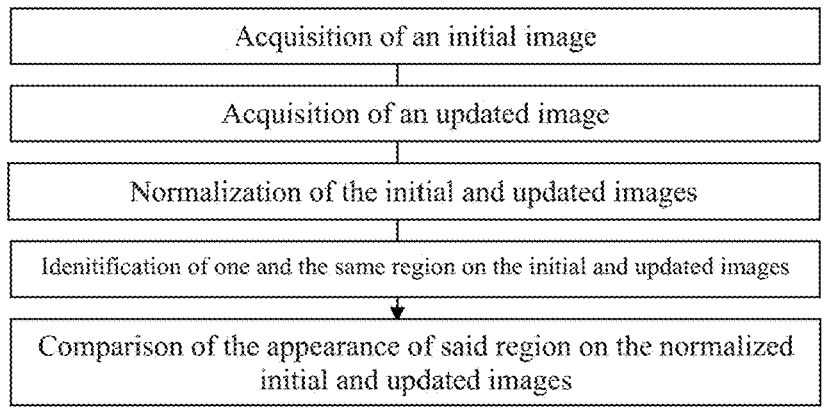
FIG. 9 represents a flow diagram illustrating the implementation of a method for monitoring the appearance of teeth according to the invention.

The invention provides a method for monitoring a property of appearance of teeth of a patient, said method comprising the steps A. to E. described above, represented in FIG. 9.

As will be seen in more detail in the description hereinbelow, this method makes it possible to assess whether the appearance, in particular the color, of one or more of the teeth has been modified, even when the acquisition conditions of the photographs of teeth of a patient are not predefined, for example because the photographs have been taken in a light environment or in any position of the acquisition apparatus, in particular by the patient.

A "property of appearance" should be understood to be a property relating to the appearance. The property of appearance can in particular be chosen from the group consisting of the color, the opalescence, the fluorescence, the gloss, the transparency, and the combinations of these properties.

"Appearance" should be understood to be a value or a set of values making it possible to quantify a property of appearance. Unless indicated otherwise, the "appearances" mentioned in the present description relate to the property of appearance that the method makes it possible to monitor.

Steps A. and B.

The steps A. and B. can be performed like the step b) described above.

The steps A. and B. are preferably performed by the patient or a near relative of the patient, but can be performed by a dentist.

The time interval between these steps can be that described above between the steps a) and b), for example greater than one week, than two weeks, than one month or than three months.

The first acquisition apparatus can be identical to or different from the second acquisition apparatus. It can be an acquisition apparatus chosen from those that can be used for the step b), notably a camera or a mobile phone.

Preferably, the acquisitions in the steps A. and/or B. are performed with the use of a flash. The results thereof are improved. Preferably, the initial and/or updated image is overexposed.

The reference gauges used for each of the steps A. and B. show a same appearance. Preferably, during each of the steps, they are arranged in the same position relative to the teeth of the patient.

Preferably, dental separators are used for each of the steps A. and B. These separators can be identical or different. Preferably, the reference gauge is borne by a separator for at least one of the steps A. and B., preferably for each of the steps A. and B. Preferably, even if the separators used for each of the steps A. and B. are different, the reference gauges are arranged on the separators in the same position relative to the aperture 14 of the separator which reveals the teeth of the patient (FIG. 5a).

Preferably, the reference gauge is arranged on the separator so as to be in proximity to the teeth whose property of appearance has to be monitored. Preferably, the reference gauge is arranged at less than 3 cm, preferably less than 2 cm, preferably less than 1 cm from the part of the separator intended to be introduced into the mouth of the patient.

Preferably, each separator comprises several reference gauges, identical or different. Preferably, several different reference gauges of one and the same separator present different appearances. The conclusions drawn from the comparison of the normalized images can advantageously be more comprehensive.

A reference gauge can for example be an identifiable point on the separator whose appearance is known, for example whose color parameters $L^*$, and/or $a^*$ and/or $b^*$, measured according to the standard NF ISO 7724, are known. The reference gauge can notably be a register mark of a separator as described above.

The acquisition conditions specify the position in space and/or the orientation of the acquisition apparatus relative to the separator.

To improve the accuracy of the appearance monitoring, it is preferable for the acquisition conditions to be substantially the same in the steps A. and B. For example, it is preferable for the two images to be taken substantially from the front. Preferably, the image acquisition apparatus used for at least one, preferably for each of the steps A. and B. comprises polarizing means facilitating the positioning thereof relative to the patient before the acquisition of the image.

The polarizing means preferably interact with register marks arranged on the separator. Preferably, the acquisition apparatus is programmed so as to, in real time, identify the register marks on the separator, analyze their relative positions or their dimensions and, consequently, inform the user of the acquisition apparatus in order for him or her to modify accordingly the position of the acquisition apparatus relative to the teeth of the patient.

These polarizing means can have one or more of the features of the polarizing means described above for the step b).

Preferably, for at least one, preferably for each of the steps A. and B., an acquisition kit according to the invention and, preferably, an acquisition method comprising steps (a) to (e) are used. Preferably, the target acquisition conditions are the same in the memory of the first and second acquisition apparatuses such that the acquisition apparatus guides its user for the initial and updated images to be taken in substantially identical acquisition conditions.

Preferably, the target acquisition conditions are determined according to the teeth whose property of appearance is to be monitored. For example, the target acquisition conditions preferably correspond to a shot taken facing the patient for a monitoring relating to an incisor and they preferably correspond to a side shot for a monitoring relating to a molar.

Step C.

The step C. consists in normalizing, that is to say "correcting", the initial image and/or the updated image so that, after correction, the representations of the reference gauge on these images present a same appearance. With the reference gauge not having changed appearance between the steps A. and B., any differences in appearance presented by the representations of the teeth on the normalized initial and updated images therefore correspond to actual differences of appearance on said teeth.

The reference gauge is first of all sought on the initial image and on the updated image. A simple image analysis is sufficient for this.

The normalization can be performed on the initial image only in order to modify the representation of the reference gauge for its appearance to be identical to that of the representation of said reference gauge on the updated image. The normalization can alternatively be performed on the updated image only in order to modify the representation of the reference gauge for its appearance to be identical to that of the representation of said reference gauge on the initial image. Finally, the normalization can be performed on the updated image and on the initial image in order to modify the representations of the reference gauges for their appearances to be identical to that of a standard gauge.

The normalization of an image is a technique well known in the field of image processing. White balance is an example of image normalization.

Step D.

Before or after the step C., it is best to identify, on each of the initial and updated images, a region of the teeth for which there is a desire to assess the change of appearance.

The use of register marks or reference gauges is possible, but remains inaccurate. Preferably, the initial and updated images are analyzed in order to represent a discriminating piece of information, of the type of those described above, for example the outline of the teeth.

The analysis of the initial and updated images can comprise one or more features of the step c), notably relating to the nature of the discriminating piece of information and to the processing to determine the discriminating piece of information. The discriminating piece of information is preferably optimized by means of an optimization method comprising steps C1 to C3.

Discriminating pieces of information common to both the initial and the updated image are then sought.

The discriminating pieces of information common to both the initial and the updated image can then be used as a reference frame to locate said region on these two images. For example, the outline of the gingiva can exhibit a succession of "points" between the teeth. This outline depends on the teeth concerned and can therefore be used as a reference frame.

In a refined embodiment, the initial and updated images are registered in relation to a reference model, preferably produced in accordance with the step a) (initial reference model) or resulting from the implementation of a method for monitoring the shape and/or the positioning of the teeth according to the invention (final reference model).

This registering can be performed as described above to register the updated image in the context of the methods for monitoring the shape and/or the positioning of the teeth. Unlike these methods, the modification of the initial reference model to arrive at the final reference model is however optional.

To register an image in relation to the reference model, it is sufficient to search for the virtual acquisition conditions in which the acquisition apparatus would have acquired said image by observing said reference model. This search is preferably performed by means of a metaheuristic method, such as those described above.

For this search, a method for assessing actual acquisition conditions according to the invention, described hereinbelow, is preferably used. This method is preferably implemented for each of the initial and updated images by means of the reference model. It makes it possible to "project" these images onto the reference model and therefore register a point of these images on the reference model.

A region of the teeth for which there is a desire to assess the change of appearance can thus be identified with great accuracy on each of the initial and updated images.

Step E.

It is then possible to measure the appearances of said region on each of the initial and updated images and compare them in order to detect and assess differences in the property of appearance.

A method for monitoring the appearance of the teeth according to the invention can be used for therapeutic or non-therapeutic purposes. It can in particular be used to:
  detect and/or measure a change of color of the teeth or the appearance and/or the evolution of spots on the teeth, or detect and/or measure a scaling of the teeth;
  check the effects on the appearance of the teeth of an eating habit or of food hygiene or of a treatment, for example, of a whitening treatment, or of a product, notably of a toothpaste, in particular for whitening the teeth or for fighting against scaling or the appearance of spots.

For example, a method for monitoring the appearance of the teeth according to the invention can be used to check the effects on the appearance of the teeth of the chewing of a chewing gum or of the ingestion of coffee or of tea, or of the consumption of tobacco or of drugs, or of brushing of the teeth.

In a preferred embodiment, it is sufficient for the patient to regularly take photographs with his or her mobile phone to constitute updated images. Preferably, using an application loaded in this telephone, he or she can then compare the appearances of the teeth on these photographs.

In one embodiment, the application normalizes the photographs in order to make them comparable, then proposes a dynamic display of the corrected photographs, for example in the form of a slide show or of a film.

Detailed Description of a Method for Assessing Actual Acquisition Conditions

Particularly for the implementation of a method for monitoring the shape, the positioning and/or the appearance of teeth according to the invention or for optimizing the quality of a discriminating piece of information, the invention provides a method for assessing, from a two-dimensional image of the dental arches of a patient, called "acquired image", the actual acquisition conditions (position of the acquisition apparatus in space, orientation of this apparatus, and, preferably, calibration of the acquisition apparatus) of said acquired image, said method comprising the following steps:

001) production of a three-dimensional digital reference model of at least a part of an arch of the patient, preferably of an arch, preferably of two arches of the patient, 002) analysis of the acquired image and production of a map relating to a discriminating piece of information, called "acquired map";

003) search for the virtual acquisition conditions approximating, optimally, said actual acquisition conditions, according to the following steps 01) to 05):

01) optionally, determination of rough virtual acquisition conditions approximating said actual acquisition conditions, preferably by analysis of the representation, on the acquired image, of a separator used during the acquisition of the acquired image;

02) determination of virtual acquisition conditions to be tested;

03) production of a two-dimensional reference image of the reference model observed in the virtual acquisition conditions to be tested;

04) processing of the reference image to produce at least one reference map representing said discriminating piece of information;

05) comparison of the acquired and reference maps so as to determine a value for an assessment function, said value for the assessment function depending on the differences between said acquired and reference maps and corresponding to a decision to continue or to stop the search for virtual acquisition conditions approximating the actual acquisition conditions with greater accuracy than said virtual acquisition conditions to be tested;

06) if said value for the assessment function corresponds to a decision to continue said search, modification of said virtual acquisition conditions to be tested, then return to the step 03);

otherwise, assessment of the actual acquisition conditions by said virtual acquisition conditions to be tested.

Preferably, the actual acquisition conditions to be assessed comprise one or more of the following calibration parameters: diaphragm aperture, exposure time, exposure time, focal distance and sensitivity.

In the assessment method, the modification made to the virtual acquisition conditions to be tested in the step 06) is preferably performed by means of a metaheuristic method, preferably evolutionist, preferably by simulated annealing, preferably by means of one of the metaheuristic methods cited previously.

An assessment method according to the invention is preferably used each time it is necessary to assess the actual acquisition conditions of an image. This image, which can in particular be an updated image acquired during a step b) or B. or an initial image acquired during a step A., is called "acquired image".

The production of the reference model in the step 001) can comprise one or more of the features, even optional, of the step a).

The acquisition of the acquired image can comprise one or more of the features, even optional, of the step b). Preferably, it implements an acquisition kit according to the invention, and preferably an acquisition method according to the invention.

The step 01) of determination of the rough virtual acquisition conditions can comprise one or more of the features, even optional, of the step c).

The steps 02) to 06) can comprise one or more of the features, even optional, of the steps e21) to e25), respectively.

Detailed Description of a Method for Optimizing a Discriminating Piece of Information A method of optimizing or "selecting" a discriminating piece of information according to the invention is intended to improve the reliability of an initial discriminating piece of information extracted from a two-dimensional image of the dental arches of a patient, or "acquired image", notably from an initial image obtained from a step A. or from an updated image obtained from a step B. or b), acquired in actual acquisition conditions. "The optimization" of the discriminating piece of information is therefore a selection of discriminating pieces of information, according to an iterative approach, so as to select from the image the discriminating piece of information most relevant for best monitoring the positioning and/or the shape of the teeth of the patient.

This method relies on a three-dimensional digital reference model of at least a part of an arch of the patient, in particular of an initial reference model from a step a).

Figure 10:
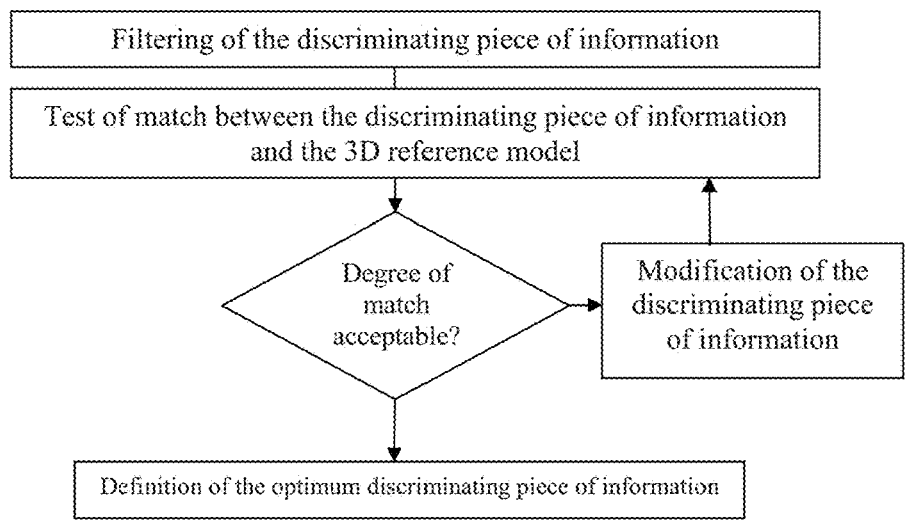
FIG. 10 represents a flow diagram illustrating the implementation of a method for optimizing a piece of discriminating information according to the invention.

As illustrated in FIG. 10, it comprises the following steps:

C1. assessment of the quality of the initial discriminating piece of information and of a quality threshold, filtering so as to retain only the initial discriminating piece of information, preferably all the initial discriminating pieces of information exhibiting a quality above the quality threshold, and definition of the "discriminating piece of information to be tested" as being the discriminating piece of information retained;

C2. testing of the matching between the discriminating piece of information to be tested and the reference model;

C3. based on the result and on a function of assessment of the result of the test:

addition of discriminating information not retained to the discriminating piece of information to be tested and/or elimination of discriminating information from the discriminating piece of information to be tested, then return to the step C2. or, definition of the optimum discriminating piece of information as being the discriminating piece of information to be tested.

The discriminating piece of information can notably be any one of the discriminating pieces of information described previously. As an example, the discriminating piece of information can be an outline information.

The initial discriminating piece of information results conventionally from the analysis of the acquired image, as described for the step c).

The methods according to the invention which use such an initial discriminating piece of information implement optimizations which provide better results if the discriminating piece of information is both abundant and of good quality. One aim of the optimization method is therefore to improve the quality of the initial discriminating piece of information.

In the step C1., the quality of the initial discriminating piece of information is assessed. In the example of an outline, the analysis of the contrast provides, for example, more or less reliable information: a zone of strong contrast can be likened to a zone corresponding to an outline with a high probability and the quality of the points of this zone will therefore be high. On the other hand, a zone of weak contrast, for example a blurred zone, can be likened to a zone corresponding to an outline with a low probability and the quality of the points of this zone will therefore be low. In this example, the probability for a point of the acquired image belonging to the outline can be chosen as indicator of the "quality" of the discriminating piece of information.

A quality threshold is used to filter the initial discriminating piece of information. If the quality threshold is high, the discriminating piece of information retained following the filtering will be of small quantity, but very reliable. If the quality threshold is low, the discriminating piece of information retained will be abundant, but unreliable. In the example of outline information, the analysis of the image will then lead to the retention of the "false" outline points, that is to say, of the points which, because of the analysis, will be considered in error as belonging to the outline of the teeth and of the gingiva.

In a preferred embodiment, the quality threshold is high in order to retain only the very reliable discriminating piece of information to be tested.

In the step C2., the match is tested, that is to say a degree of match is determined, between the discriminating piece of information to be tested and the reference model.

Preferably, an "acquired" map of the discriminating piece of information to be tested resulting from the processing of the acquired image is produced.

Preferably, the method then continues according to the steps 01) to 06), and in particular the following steps:
02) determination of virtual acquisition conditions to be tested;
03) production of a two-dimensional reference image of the reference model observed in the virtual acquisition conditions to be tested;
04) processing of the reference image to produce at least one reference map representing discriminating information;
05) comparison of the acquired and reference maps so as to determine a value for an assessment function, said value for the assessment function depending on the differences between said acquired and reference maps and corresponding to a decision to continue or to stop the search for virtual acquisition conditions approximating the actual acquisition conditions with greater accuracy than said virtual acquisition conditions to be tested;
06) if said value for the assessment function corresponds to a decision to continue said search, modification of said virtual acquisition conditions to be tested, then return to the step 03); otherwise, assessment of the actual acquisition conditions by said virtual acquisition conditions to be tested.

In the step 04), the processing of the reference image makes it possible to produce a reference map representing said discriminating piece of information. The criteria for selecting the discriminating piece of information represented on the reference map can be identical or different from those used to select the discriminating piece of information to be tested.

Preferably, the discriminating piece of information represented on the reference map is selected with the same criteria as the discriminating piece of information to be tested. In the example of an outline, the processing of the reference image can consist in retaining the points of the reference image corresponding to an outline with a high probability.

The probability for a point of the reference image belonging to the outline can be determined as for the processing of the acquired image and also serve as indicator of the quality of the discriminating piece of information. The quality threshold can also be identical to the one used for the processing of the acquired image. The outline represented on the reference map is then similar to that represented on the acquired map, and in particular exhibits a substantially identical length.

The steps 01) to 06) make it possible to determine, with the reference model, virtual acquisition conditions approximating the actual acquisition conditions of the acquired image.

The observation of the reference model in these virtual acquisition conditions therefore provides a view which best corresponds to the acquired image. The search for the virtual acquisition conditions is however based on the discriminating piece of information to be tested. The degree of correspondence therefore depends on the discriminating piece of information to be tested. The higher the quality and quantity of the discriminating piece of information to be tested, the better the degree of correspondence between the view of the reference model in the virtual acquisition conditions and the acquired image, and the higher the degree of match between the discriminating piece of information to be tested and the reference model.

The degree of match can for example be measured by the inverse of the deviation between
the reference map relating to the image of the reference model observed in the virtual acquisition conditions best approximating the actual acquisition conditions following the execution of the steps 01) to 06), and
the "acquired" map representing the discriminating piece of information to be tested corresponding to the acquired image weighted by the quantity of discriminating information to be tested.

For an outline for example, the degree of match can be the ratio of the number of points which belong to both the outline of the reference map and the outline of the acquired map, to the total number of points of the outline of the acquired map, or the product of the inverse of the mean distance between the outlines represented on said acquired and reference maps, and the length of the outline represented on the acquired map.

The "best" approximation of the actual acquisition conditions from a discriminating piece of information to be tested can be assessed by a result or "score", for example by the degree of match. The aim of the cycle of the steps C2. and C3. is to optimize this result by acting on the discriminating piece of information to be tested.

This optimization is similar to that implemented for the methods for monitoring the positioning and/or the shape of the teeth. These methods however act on the initial reference model, by movement of the tooth models and/or by deformation of the reference model, whereas the method for optimizing the discriminating piece of information acts on the discriminating piece of information used to establish the acquired map.

The operation performed in the step C3. is determined by a function of assessment of the result of the test of the step C2. Preferably, the assessment function takes into account results obtained during preceding C2.-C3. cycles.

In particular, the method can be stopped if the assessment function indicates that the continuation of C2.-C3. cycles does not make it possible to improve the result, for example because one or more C2.-C3. cycles have not made it possible to improve it or have not made it possible to improve it significantly. The discriminating piece of information tested during the C2.-C3. cycle having led to the best result is then considered as optimal.

Otherwise, a new C2.-C3. cycle can be launched, after modification of the discriminating piece of information to be tested. The modification to be made to the discriminating piece of information which has just been tested can consist in an addition or a elimination of discriminating information. An addition of discriminating information can for example be decided if the last result is the best obtained hitherto and if, according to the assessment function, the result can be further improved. Preferably, the discriminating piece of information added is that which, out of the discriminating piece of information not retained in the step C1. and which has not yet been tested, exhibits the best quality. For example, when the discriminating piece of information is outline information, the addition of discriminating information can consist in adding points of the image not retained initially, never yet added and whose quality, as assessed in the step C1., is the highest, that is to say whose addition is the most likely to improve the result of the test of the step C2.

An elimination of discriminating information can for example be decided if the last result is worse that the preceding one. In particular, the discriminating piece of information added during the preceding cycle can be deleted and an addition of another discriminating piece of information can be performed, as described previously.

The determination of the discriminating piece of information to be added and/or deleted can be random. However, preferably, it results from the implementation of a metaheuristic method, preferably evolutionist, preferably by simulated annealing, preferably of the type of those described above.

Example

Figure 11:
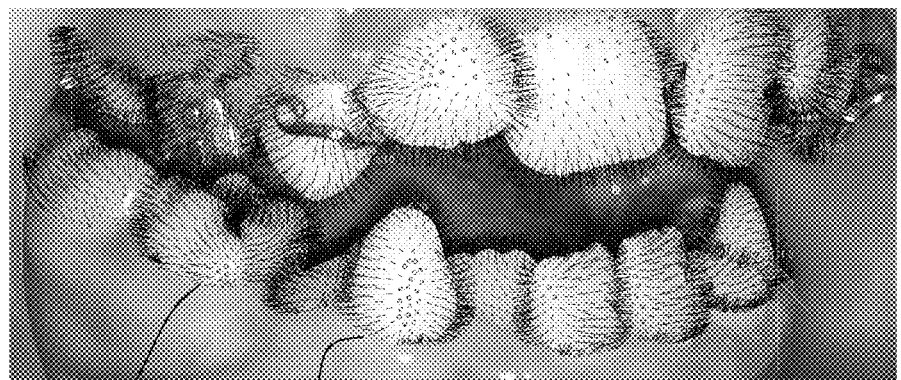
FIG. 11 represents, on an acquired image, a reference map established for a glare information.

As an example, FIG. 11 represents, superimposed on the acquired image, a reference map relating to a glare information (discriminating information). The acquired image, preferably acquired by an acquisition kit according to the invention, is a photograph taken in a particular position and orientation of the camera. This position and this orientation constitute the actual acquisition conditions of the acquired image.

A person skilled in the art knows that, on the acquired image, the higher the brightness of a point, the higher the probability that this point belongs to a glare zone. The brightness can therefore be used as indicator of the "quality" of the glare information.

The filtering in the step C1. can consist in retaining only the zones of the acquired image which exhibit a brightness above a quality threshold, for example of 70%.

The acquired map represents these zones, which constitute the discriminating piece of information to be tested.

In the step C2., a test as to whether the zones retained match with the observation of the reference model is performed, preferably according to the steps 01) to 06).

In the step 01), the acquired image is analyzed to roughly assess the actual acquisition conditions by virtual acquisition conditions. This assessment results preferably from an analysis of the position and/or of the shape of the representation, on the acquired image, of register marks of a separator used during the acquisition.

The roughly assessed virtual acquisition conditions can constitute the "virtual acquisition conditions to be tested" in the step 02).

In the step 03), by observing the reference model from virtual acquisition conditions to be tested, a reference image is obtained.

In the step 04), as represented in FIG. 11, it is possible to project, onto the reference image, vectors (black lines 20), all of the same length, at right angles to the faces of the reference model. The circles 22 represent these vectors when they are observed according to their length. The reference map is thus made up of these black lines 20 and circles 22.

A person skilled in the art knows that these circles 22 normally correspond to zones of the image corresponding to glare. On the reference map, the discriminating piece of information, namely the glare information, is therefore represented by the black lines 20 and by the circles 22, the inverse of the length of the black lines being able to be used as indicator of the "quality" of the glare information on the reference map, a circle corresponding to a zero length, and therefore to a maximum quality.

In the step 05), a comparison of the acquired and reference maps can for example consist in checking whether the lines 20 and the circles 22 are within zones of the acquired map (which correspond initially to a brightness greater than 70%). The assessment function can for example be the ratio R between the difference between the number of circles 22 and the number of lines which are inside zones of the acquired image and the total number of circles 22.

The decision can be to continue the search by modifying the virtual acquisition conditions to be tested until a maximum is reached for the acquisition function.

In the step 06), if this maximum is considered to be reached, the loop of the steps 03) to 06) is exited. Otherwise, a modification to be made to the virtual acquisition conditions to be tested is determined, preferably by means of a metaheuristic method, preferably evolutionist, and there is a return to the step 03).

On exiting the steps 03) to 06), the ratio R is therefore maximal, for this acquired image, for example 95%. This ratio R then represents the result of the match test performed in the step C2.

In the step C3, this result is assessed by means of an assessment function. This assessment function preferably determines whether the result is optimal or not. If the result is considered optimal, for example because no better result can now be obtained after several cycles of the steps C2.-C3., it is considered that the zones of the corresponding acquired map constitute optimal discriminating information.

Otherwise, the acquired map is modified, for example by adding points of the acquired image, for example by adding points which exhibit a brightness greater than 71%. This addition leads to the addition of circles in the zones of the acquired map, which improves the ratio R, but also to the addition of black lines, which degrades the ratio R. On the other hand, it is possible to extract the points which exhibit a brightness greater than 69%. This elimination leads to the elimination of circles in the zones of the acquired map, which degrades the ratio R, but also leads to the elimination of black lines, which improves the ratio R.

The modification to be made is preferably guided by a metaheuristic method, preferably evolutionist.

From the new acquired map, which defines the discriminating piece of information to be tested, there is a return to the step C2.

The cycling of the steps C2. and C3. can be continued until an optimal result is determined. The discriminating piece of information to be tested is then considered optimal.

As now clearly emerges, a method for optimizing a discriminating piece of information according to the invention makes it possible to construct a discriminating piece of information that is of good quality and abundant. In particular, it makes it possible, from a partial initial outline, but of good quality, to gradually construct an outline that is more complete but still of good quality.

Obviously, the invention is not limited to the embodiments described above and represented.

In particular, unless indicated otherwise, the optional features described in the context of a step of a first method according to the invention are applicable in the context of a similar step or one bearing the same reference of a second method according to the invention.

The method for monitoring the positioning and/or the shape of the teeth can be implemented successively for each of the two arches or simultaneously for the two arches. Furthermore, for these methods, several different apparatuses can be implemented. For example, the acquisition can be performed with a mobile phone and the subsequent steps with a fixed computer.

Finally, the patient is not limited to a human being. In particular, a method for monitoring the positioning of teeth according to the invention can be used for another animal.

The invention claimed is:

1. A method for monitoring a property of appearance of teeth of a patient, said method comprising the following successive steps:
   A. acquisition, by means of a first acquisition apparatus and a first dental separator, of at least one first two-dimensional image of said teeth and of a first reference gauge, called "initial image";
   B. acquisition, by means of a second acquisition apparatus and a second dental separator, of at least one second two-dimensional image of said teeth and of a second reference gauge exhibiting a same appearance as the first reference gauge, called "updated image";
   C. normalization, by computer, of the initial and updated images so that the representations of the first and second reference gauges on the normalized initial and updated images exhibit a same appearance;
   D. before or after the step C., identification, by computer, of a same region of the teeth on the initial and updated images; and
   E. comparison, by computer, of the property of appearance of said region on the normalized initial and updated images,
   wherein:
      the second acquisition apparatus is a mobile phone and the updated image is a photograph taken by the patient with the mobile phone,
      the property of appearance is one or more of a color, an opalescence, a fluorescence, a gloss, and a transparency.

2. The method as claimed in claim 1, in which the time interval between the steps A. and B. is greater than one week.

3. The method as claimed in claim 1, in which the first acquisition apparatus is a camera and/or mobile phone, the acquisitions in the steps A. and/or B. being performed under flash lighting.

4. The method as claimed in claim 1, in which the acquisitions in the steps A. and/or B. are performed by means of an acquisition kit comprising:
   at least one of the first and the second dental separators intended to be placed in the mouth of a patient and comprising at least one register mark;
   at least one of the first and the second image acquisition apparatuses comprising:
      a display screen,
      a computer memory containing information on target acquisition conditions,
      a computer program comprising program code instructions for simultaneously displaying, on said screen, a preview image and a reference, said reference being in a position such that, when the register mark matches the reference on the screen, the acquisition apparatus meets target acquisition conditions.

5. The method as claimed in claim 4, in which the target acquisition conditions are determined according to the teeth whose property of appearance is to be monitored.

6. The method as claimed in claim 4, in which the acquisitions in the steps A. and B. are performed by means of acquisition kits in which the target acquisition conditions are identical.

7. The method as claimed in claim 4, in which the first and/or the second acquisition apparatus comprises a computer program comprising program code instructions for identifying, in real time, the at least one register mark on the first and/or the second separator, analyzing its or their positions or dimensions and, accordingly, supplying a piece of information.

8. The method as claimed in claim 1, in which, in the step D., the identification comprises a comparison of discriminating pieces of information common to both the initial and the updated image, then an identification of said region relative to said common discriminating pieces of information.

9. The method as claimed in claim 1, in which, in the step D., the identification of said region on the initial and/or updated images comprises a search for virtual acquisition conditions in which the first acquisition apparatus and/or the second acquisition apparatus, respectively, would have acquired said initial and/or updated image by observing a three-dimensional digital reference model of at least a part of an arch of the patient.

10. The method as claimed in claim 1, in which, in the step D., the identification of the region on the initial and/or updated image, called "acquired image", comprises the implementation of a method for assessing the actual acquisition conditions of the acquired image, said method comprising the following steps:
   001) production of a three-dimensional digital reference model of at least a part of an arch of the patient;
   002) analysis of the acquired image and production of a map relating to a discriminating piece of information, called "acquired map";
   003) search for the virtual acquisition conditions approximating, optimally, said actual acquisition conditions, according to the following steps 01) to 05):
      01) determination of virtual acquisition conditions to be tested;
      02) production of a two-dimensional reference image of the reference model observed in the virtual acquisition conditions to be tested;
      03) processing of the reference image to produce at least one reference map representing said discriminating piece of information;
      04) comparison of the acquired and reference maps so as to determine a value for an assessment function, said value for the assessment function depending on the differences between said acquired and reference maps;

05) depending on said value for the assessment function, modification of said virtual acquisition conditions to be tested, then return to the step 02); or assessment of the actual acquisition conditions by said virtual acquisition conditions to be tested.

11. The method as claimed in claim 1, in which an application is loaded in said mobile phone and configured for said patient to compare the appearances of said teeth on photographs he or she takes to constitute updated images.

12. The method as claimed in claim 1, in which the first and second reference gauges are borne by the first and second dental separators, respectively.

* * * * *